United States Patent
Chen et al.

(10) Patent No.: US 11,266,728 B2
(45) Date of Patent: Mar. 8, 2022

(54) COMPOSITIONS AND METHODS FOR ENHANCEMENT OF IMMUNE RESPONSES

(71) Applicant: NATIONAL HEALTH RESEARCH INSTITUTES, Zhunan (TW)

(72) Inventors: Hsin-Wei Chen, Zhunan (TW); Chih-Hsiang Leng, Zhunan (TW); Shih-Jen Liu, Zhunan (TW)

(73) Assignee: NATIONAL HEALTH RESEARCH INSTITUTES, Zhunan (TW)

( * ) Notice: Subject to any disclaimer, the term of this patent is extended or adjusted under 35 U.S.C. 154(b) by 204 days.

(21) Appl. No.: 16/475,963

(22) PCT Filed: Dec. 29, 2017

(86) PCT No.: PCT/US2017/068989
§ 371 (c)(1),
(2) Date: Jul. 3, 2019

(87) PCT Pub. No.: WO2018/128931
PCT Pub. Date: Jul. 12, 2018

(65) Prior Publication Data
US 2019/0321456 A1 Oct. 24, 2019

Related U.S. Application Data

(60) Provisional application No. 62/441,682, filed on Jan. 3, 2017.

(51) Int. Cl.
| | |
|---|---|
| *A61K 39/00* | (2006.01) |
| *C07K 16/28* | (2006.01) |
| *A61K 39/395* | (2006.01) |
| *A61K 39/39* | (2006.01) |
| *A61K 45/06* | (2006.01) |
| *A61K 39/12* | (2006.01) |
| *C07K 14/705* | (2006.01) |

(52) U.S. Cl.
CPC ...... *A61K 39/00115* (2018.08); *A61K 39/001168* (2018.08); *A61K 39/12* (2013.01); *C07K 14/705* (2013.01); *C07K 2319/00* (2013.01)

(58) Field of Classification Search
CPC .......... A61K 39/3955; A61K 2039/505; A61K 2300/00; A61P 35/00; A61P 35/02
See application file for complete search history.

(56) References Cited

PUBLICATIONS

Bitsaktsis et al., "Mucosal Immunization with an Unadjuvanted Vaccine That Targets *Streptococcus pneumoniae* PspA to Human Fc Receptor Type I Protects against Pneumococcal Infection through Complement- and Lactoferrin-Mediated Bactericidal Activity", Infection and Immunity, 2011, 80(3):1166-1189.*

Bitsaktsis et al., "Mucosal Immunization with an Unadjuvanted Vaccine That Targets *Streptococcus pneumoniae* PspA to Human Fc Receptor Type 1 Protects against Pneumococcal Infection through Complement- and Lactoferrin-Mediated Bactericidal Activity", Infection and Immunity, 2011, 80(3): 1166-1189.*

Stemerding et al., "*Staphylococcus aureus* Formyl Peptide Receptor-like 1 Inhibitor (FLIPr) and Its Homologue FLIPr-like Are Potent FcgR Antagonists That Inhibit IgG-Mediated Effector Functions", The Journal of Immunology, 2013: 191 (1):353-362.*

Bitsaktsis, et al. "Mucosal Immunization with an Unadjuvanted Vaccine That Targets *Streptococcus pneumoniae* PspA to Human FcγReceptor Type I Protects against Pneumococcal Infection through Complement- and Lactoferrin-Mediated Bactericidal Activity"; Infection and Immunity, Mar. 2012, vol. 80, No. 3, pp. 1166-1180 (XP055507945).

Stemerding et al.; "*Staphylococcus aureus* Formyl Peptide Receptor-like 1 Inhibitor (FLIPr) and Its Homologue FLIPr-like Are Potent FcγR Antagonists That Inhibit IgG-Mediated Effector Functions" The Journal of Immunology, The American Association of Immunologists, Inc, Jul. 1, 2013 vol. 191, pp. 353-362 (XP055507948).

Garg, Himani, et al.; "Survivin: a unique target for tumor therapy"; Cancer Cell International, Dec. 1, 2016, vol. 16, pp. 1-14 (XP-055507953).

* cited by examiner

*Primary Examiner* — Barry A Chestnut
(74) *Attorney, Agent, or Firm* — Muncy, Geissler, Olds & Lowe, P.C.

(57) ABSTRACT

Provided is a pharmaceutical composition, including an antigen fusion protein which includes an antigen and an antagonist of an Fc gamma receptor. Also provided is a method of enhancing immunogenicity of an antigen, including conjugating the antigen with an antagonist of an Fc gamma receptor to form an antigen fusion protein. Also provided is a method of enhancing an immune response to an antigen in a subject, including administering to the subject an effective amount of an antigen fusion protein which includes an antigen and an antagonist of an Fc gamma receptor. The present invention may be applied in the development of potent vaccines based on targeting vaccine antigens to antigen-presenting cells via binding to Fc gamma receptors.

12 Claims, 15 Drawing Sheets

Specification includes a Sequence Listing.

COMPOSITIONS AND METHODS FOR ENHANCEMENT OF IMMUNE RESPONSES

CROSS-REFERENCES TO RELATED APPLICATIONS

This application claims priority of Provisional Application No. 62/441,682, filed on Jan. 3, 2017, the content of which is incorporated herein in its entirety by reference.

BACKGROUND OF THE INVENTION

1. Field of the Invention

The present invention relates to a composition and a method for modulation of immune responses. Particularly, the present invention relates to a pharmaceutical composition and a method for enhancement of immune responses using an antigen fusion protein containing an antigen and an antagonist to an Fc gamma receptor.

2. The Prior Art

Immunogenicity of vaccine antigens is a major concern for vaccine development because the potential of a vaccine to prevent or treat diseases highly depends on the ability of the vaccine antigens to effectively induce immune responses. One strategy commonly used to increase immunogenicity of vaccines is addition of adjuvants into the vaccine formulations. Adjuvants are immune-augmenting substances of heterogeneous types, and they act through a variety of mechanisms, including prolonging the release time of antigens from the injection site, providing a vehicle for antigen transport throughout the lymphatic system, and acting as immunostimulants. Though adjuvants effectively enhance immune responses, many of them may cause unwanted hypersensitivity reactions.

An alternative to efficiently induce immune responses is to directly stimulate antigen-presenting cells. Professional antigen-presenting cells capture and process antigens in the peripheral tissue, express lymphocyte co-stimulatory molecules, migrate to lymphoid organs, and secrete cytokines to initiate immune responses. Dendritic cells, the most potent antigen-presenting cells, play a critical role during the initiation of adaptive immune responses, leading to differentiation of naïve T cells ($CD4^+$ or $CD8^+$ T cells) into effector cells (helper or cytotoxic T cells) and further regulation of humoral immune responses. These characteristics have made dendritic cells as prime targets for immune-modulation strategies.

Antigen-presenting cells express various Fc gamma receptors (FcγRs), which mediate internalization of antigen-antibody complexes (also termed immune complexes) and regulate immune responses. FcγRs are divided into activating receptors, such as FcγRI, FcγRIIA, FcγRIII, and FcγRIV, and inhibitory receptors, such as FcγRIM, according to the function of FcγRs. Previous reports have shown that immune complexes are efficient in induction of immune responses through the engagement of FcγRs on dendritic cells. However, it is costly to employ the immune complexes in vaccine development since preparation of antibodies and the associated immune complexes is expensive and complicated.

Accordingly, there is a need to develop a novel strategy to enhance antigen-specific immune responses by targeting the antigen to antigen-presenting cells without the use of immune complexes.

SUMMARY OF THE INVENTION

As a result, the present invention provides a pharmaceutical composition, including an antigen fusion protein which includes an antigen and an antagonist of an Fc gamma receptor (FcγR).

In another aspect, the present invention provides a method of enhancing immunogenicity of an antigen, including conjugating the antigen with an antagonist of an Fc gamma receptor to form an antigen fusion protein.

In one further aspect, the present invention provides a method of enhancing an immune response to an antigen in a subject, including administering to the subject an effective amount of an antigen fusion protein, wherein the antigen fusion protein includes the antigen and an antagonist of an Fc gamma receptor.

In one embodiment of the present invention, the antagonist of the Fc gamma receptor is a formyl peptide receptor-like 1 inhibitory protein (FLIPr) or a FLIPr-like protein.

In another embodiment of the present invention, the antigen is a polypeptide derived from a cancer cell or a virus. The antigen may be selected from the group consisting of survivin, mesothelin, and Zika virus envelope protein domain III.

In yet another embodiment, the immune response includes an increase in $CD4^+$ T cells, $CD8^-$ T cells, or combinations thereof, the secretion of a cytokine selected from the group consisting of interferon gamma (IFN-γ), interleukin-2 (IL-2), interleukin-5 (IL-5), interleukin-17A (IL-17A), and combinations thereof, and the production of antigen-specific immunoglobulin G (IgG) antibodies.

The pharmaceutical composition of the present invention utilize the antigen fusion protein which targets antigens to antigen-presenting cells via binding to FcγRs to augment antigen-specific immune responses in a subject, leading to increasing numbers of antigen-specific $CD4^+$ T cells and $CD8^+$ T cells, and elevated levels of proinflammatory cytokines and antigen-specific antibodies. The provided methods of enhancing immunogenicity of an antigen and enhancing immune responses to an antigen in a subject are simple and may be applied in the development of potent vaccines, such as antitumor and antivirus vaccines, without the use of additional adjuvant or immune complexes. Since the present invention increases the efficacy of vaccine antigens, it provides a strategy to elicit efficient immune responses in subjects with compromised immunity, such as elderly patients.

The present invention is further explained in the following drawings and examples. It is understood that the examples given below do not limit the scope of the invention, and it will be evident to those skilled in the art that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which:

FIG. 1A shows an image of a polyacrylamide gel displaying purified recombinant proteins, including an ovalbumin (OVA) and two OVA fusion proteins fusing OVA with formyl peptide receptor-like 1 inhibitory protein (OVA-FLIPr) or with FLIPr-like protein (OVA-FLIPr-like), respectively;

FIG. 1B shows detection of the purified recombinant proteins, including the OVA, the OVA-FLIPr fusion protein, and the OVA-FLIPr-like fusion protein, by western blotting using an anti-OVA antibody;

DETAILED DESCRIPTION OF THE PREFERRED EMBODIMENT

Definition

Figure 1A:
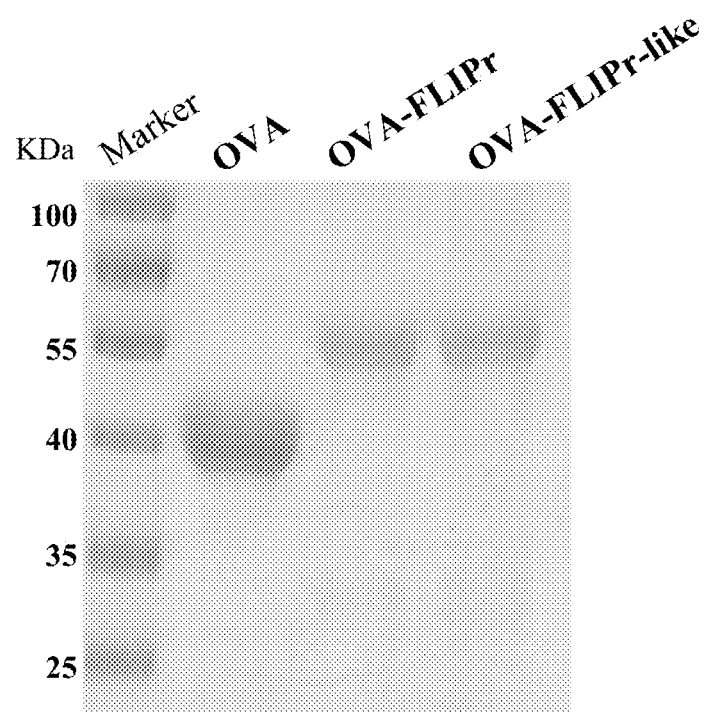

Numerical quantities given herein are approximate, and experimental values may vary within 20 percent, preferably within 10 percent, and most preferably within 5 percent. Thus, the terms "about" and "approximately" refer to within 20 percent, preferably within 10 percent, and most preferably within 5 percent of a given value or range.

As used herein, the term "immunogenicity" refers to the ability of an antigen to elicit or induce an immune response. An antigen which causes a greater immune response is of higher immunogenicity.

The present invention relates to a pharmaceutical composition, which contains an antigen fusion protein including an antigen and an antagonist of an Fc gamma receptor, and a method of enhancing immune responses to an antigen in a subject, including administering to the subject an effective amount of the antigen fusion protein for immunization. In the following examples, ovalbumin (OVA), survivin (Sur), mesothelin, and Zika virus envelope protein domain III (ZE3) were used as exemplary antigens for investigation of the immune-augmenting effects of the antigen fusion protein of the present invention. The formyl peptide receptor-like 1 inhibitory protein (FLIPr; SEQ ID NO:1) and its homolog FLIPr-like (SEQ ID NO:2), which are potent FcγR antagonists secreted by *Staphylococcus aureus* to evade FcγR-mediated host immunity, are the exemplary antagonists of the FcγRs for preparation of the FLIPr- or FLIPr-like-containing fusion proteins.

Methods and Materials

Cloning and Expression of the Antigen Fusion Proteins

The FLIPr or the FLIPr-like segment of the antigen fusion protein was preferably conjugated to the C-terminus of an antigen, such as OVA, survivin, and ZE3, via a peptide linker composed of three repeats of 4 glycine residues and 1 serine residue. According to the amino acid sequences of OVA (SEQ ID NO:3), OVA-FLIPr fusion protein (SEQ ID NO:4), OVA-FLIPr-like fusion protein (SEQ ID NO:5), survivin (SEQ ID NO:6), survivin-FLIPr (Sur-FLIPr) fusion protein (SEQ ID NO:7), mesothelin (SEQ ID NO:8), mesothelin-FLIPr fusion protein (SEQ ID NO:9), ZE3 (SEQ ID NO:10), and ZE3-FLIPr fusion protein (SEQ ID NO:11), the corresponding nucleotide sequences were determined based on Escherichia coli codon usage and the DNA with each of these nucleotide sequences were fully synthesized. The synthesized DNA was then amplified by polymerase chain reaction (PCR). The PCR products were cloned into the NdeI and XhoI sites of an expression vector pET-22b(+) to generate expression plasmids of the antigens or the antigen fusion proteins. These plasmids were used to produce the recombinant antigens and antigen fusion proteins.

For preparation of the recombinant proteins, E. coli BL21 (DE3) was transformed with each of the abovementioned expression plasmids. The transformed cells were cultured at 37° C. overnight, and protein expression was induced by adding 1 mM isopropyl β-D-1-thiogalactopyranoside (IPTG), followed by incubation at 37° C. for 3 hours. Next, the transformed cells were lysed by a French press (Constant Systems, Daventry, UK) at 27 Kpsi in a homogenization buffer (20 mM Tris (pH 8.0), 50 mM sucrose, 500 mM NaCl, 10% glycerol). The cell lysate were then centrifuged at 80,000 xg for 40 minutes to obtain a cell pellet containing inclusion bodies. Most of the recombinant proteins were present in inclusion bodies and were solubilized with an extraction buffer (50 mM $NaH_2PO_4$, 5 mM ethylenediaminetetraacetic acid (EDTA), 200 mM NaCl, 0.5 M urea, 1% Triton X-100, pH 6.0). The recombinant proteins were purified by loading the extracted fraction onto an immobilized metal affinity chromatography column (QIagen, Hilden, Germany).

Enzyme-Linked Immunosorbent Assay (ELISA) for FcγR Binding

To detect the binding of the recombinant antigens or antigen fusion proteins to FcγR subclasses, 96-well plates were coated overnight at 4° C. with 0.1 mL recombinant proteins at 1 µg/mL in phosphate buffered saline (PBS; sodium chloride 137 mM, potassium chloride 2.7 mM, sodium hydrogen phosphate 10 mM, and potassium dihydrogen phosphate 1.8 mM, pH 7.4). The plates were washed three times with PBS supplemented with 0.05% v/v Tween 20 and incubated with a serial dilution of various biotin-conjugated recombinant FcγR proteins, including FcγRI, FcγRIIa-H131, FcγRIIb, FcγRIIIa-V158, FcγRIIIa-F158, and FcγRIIA. After incubation at room temperature for 2 hours, the plates were washed and incubated for 30 min with horseradish peroxidase (HRP)-conjugated streptavidin. For detection of the FcγR binding, 3, 3', 5, 5'-tetramethylbenzidine (TMB) was added to the plates and the absorbance at 450 nm was measured with an ELISA reader.

Animal Studies

Female C57BL/6 mice were purchased from the National Laboratory Animal Center. All the mice were housed at the Laboratory Animal Center of the National Health Research Institutes (Taiwan). All the animal studies were approved and were performed in compliance with the guidelines of the Animal Committee of the National Health Research Institutes. For immunization, mice were arbitrarily assigned to groups and subcutaneously administered twice with the recombinant antigens or antigen fusion proteins at a two-week interval.

Enzyme-Linked Immunospot (ELISPOT) Assay

The number of IFN-γ-producing cells was determined using mouse IFN-γELISPOT kits. Briefly, 96-well plates with polyvinylidene difluoride (PVDF) membranes were first coated with capture antibody and incubated at 4° C. for 18 hours. The plates were washed twice and blocked with RPMI medium supplemented with 10% fetal bovine serum (FBS) for one hour to prevent nonspecific binding in later steps. Splenocytes from the immunized mice were seeded at a density of $5 \times 10^5$ cells/well and stimulated with one of the indicated peptides.

The splenocytes from the mice immunized with the OVA or the OVA fusion proteins were stimulated with an OVA peptide termed OT-1 (SIINFEKL; SEQ ID NO:12), another OVA peptide termed OT-2 (ISQAVHAAHAEINEAGR; SEQ ID NO:13), a control peptide for OT-1 peptide (RAHYNIVTF; SEQ ID NO:14), or a control peptide for OT-2 peptide (GRLITVNPIVTEKDS; SEQ ID NO:15) and incubated for two days.

The splenocytes from the mice immunized with the survivin or the survivin fusion protein were stimulated with 10 µg/mL of a survivin peptide termed survivin21-29; SEQ ID NO:16), another survivin peptide termed survivin57-64; SEQ ID NO:17), or a control RAH peptide (SEQ ID NO:14) and incubated for three days.

After incubation, the splenocytes were removed from the plates by washing three times with 0.05% (w/v) Tween 20 in PBS. A 100 µL aliquot of biotinylated detection antibody was added to each well. The plates were incubated at 37° C. for 2 hours. The washing steps were repeated as above, and after a 45-minute incubation at room temperature with the avidin-HRP complex reagent, the plates were washed three times with 0.05% (w/v) Tween 20 in PBS and then three times with PBS alone. A 100 µL aliquot of 3-amine-9-ethyl carbazole (Sigma-Aldrich) staining solution was added to each well to develop the spots. The reaction was stopped after one hour by placing the plates under tap water. The spots were counted using an ELISPOT reader (Cellular Technology Ltd.)

In Vivo Cytotoxicity Assay

Splenocytes from naive C57BL/6 mice were divided into two populations. One population was pulsed with 10 µM OT-1 peptide at 37° C. for 90 min. These cells were labeled with carboxyfluorescein succinimidyl ester (CFSE) at a final concentration of 10 µM ($CFSE^{high}$) at 37° C. for 15 min. In parallel, the other population was pulsed with a control peptide for OT-1 (SEQ ID NO:14) and labeled with 1 µM CFSE ($CFSE^{low}$). The two populations were mixed equally and $2 \times 10^7$ cells were injected intravenously into the immunized mice. After 24 hours, single cells from spleen were isolated and CFSE intensities were analyzed using FACSCalibur flow cytometer and CellQuest Pro software. The percentage of specific killing was calculated as follows: % specific killing=[1-(% $CFSE^{high}$/% $CFSE^{high}$ before injection)/(% $CFSE^{low}$/% $CFSE^{low}$ before injection)].

EG7 Tumor Model

Tumor-bearing mice were established by inoculating EG7 cells into mice via subcutaneous injection before or after immunization with the antigen fusion protein. The EG7 tumor cells are derived from EL4 cells, a mouse lymphoma cell line. The presence or absence of tumor was assessed by visual inspection and palpation. Tumor size was measured three times per week with a caliper, and mice were sacrificed when tumor volume reached 3000 $mm^3$. Tumor volume was estimated as follows: tumor volume=tumor width×tumor length×(tumor width+tumor length)/2.

Example 1

Preparation and FcγR Binding of the OVA Fusion Proteins

The DNA encoding OVA, OVA-FLIPr fusion protein, or OVA-FLIPr-like fusion protein was synthesized, amplified by PCR, and cloned into a pET-22b-based vector to generate the expression plasmid pOVA, pOVA-FLIPr, or pOVA-FLIPr-like. *E. coli* were then transformed with each of the plasmids for protein expression. After purification with immobilized metal affinity chromatography, the successful production of the recombinant proteins was verified by sodium dodecyl sulfate polyacrylamide gel electrophoresis (SDS-PAGE) and western blotting.

Figure 1B:
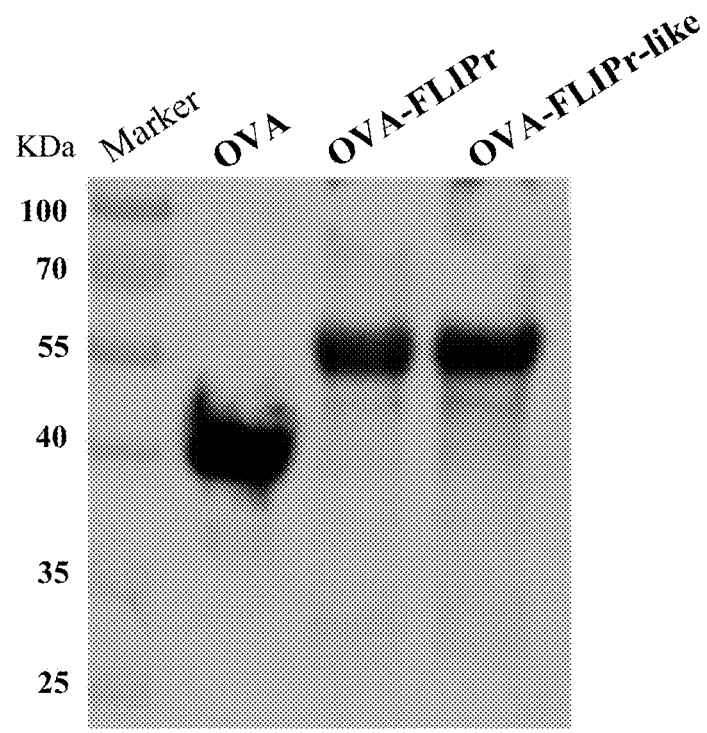

As shown in FIG. 1A, the recombinant OVA, OVA-FLIPr fusion protein, and OVA-FLIPr-like fusion protein were visualized on the polyacrylamide gel stained with Coomassie brilliant blue. As shown in FIG. 1B, the recombinant OVA, OVA-FLIPr fusion protein, and OVA-FLIPr-like fusion protein were detected by western blotting using the anti-OVA antibody.

Figure 2A:
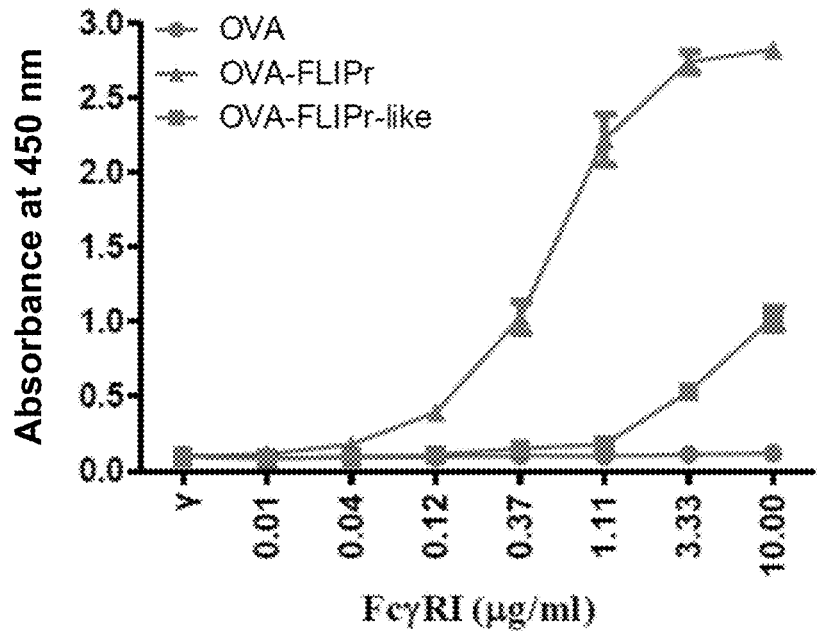
FIG. 2A shows the binding of FcγRI to the recombinant proteins, including the OVA, the OVA-FLIPr fusion protein, and the OVA-FLIPr-like fusion protein.
Figure 2B:
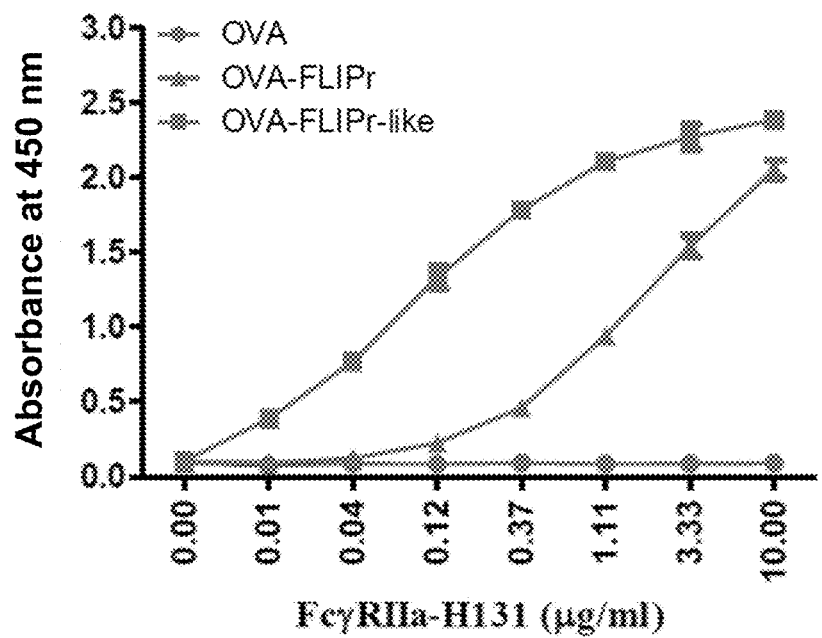
FIG. 2B shows the binding of FcγRIIa-H131 to the recombinant proteins, including the OVA, the OVA-FLIPr fusion protein, and the OVA-FLIPr-like fusion protein.
Figure 2C:
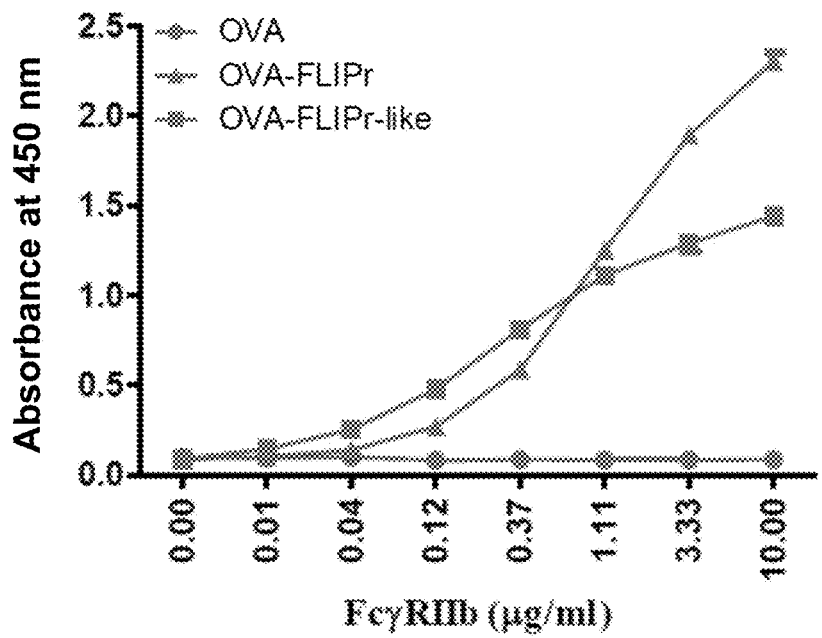
FIG. 2C shows the binding of FcγRIIb to the recombinant proteins, including the OVA, the OVA-FLIPr fusion protein, and the OVA-FLIPr-like fusion protein.
Figure 2D:
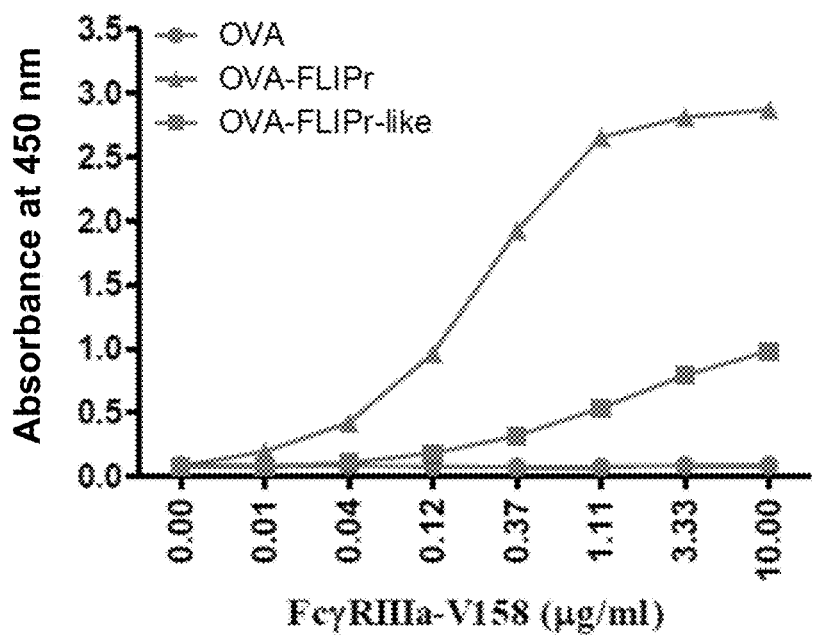
FIG. 2D shows the binding of FcγRIIIa-V158 to the recombinant proteins, including the OVA, the OVA-FLIPr fusion protein, and the OVA-FLIPr-like fusion protein.
Figure 2E:
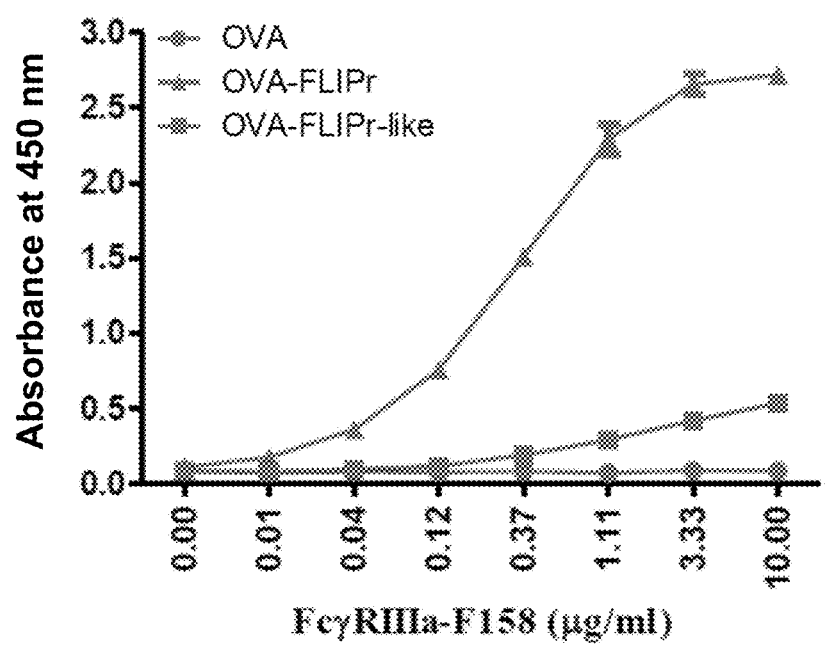
FIG. 2E shows the binding of FcγRIIIa-F158 to the recombinant proteins, including the OVA, the OVA-FLIPr fusion protein, and the OVA-FLIPr-like fusion protein.

To analyze the functional activity of the recombinant OVA-FLIPr fusion protein and OVA-FLIPr-like fusion protein, a capture ELISA was performed to confirm that both of the OVA fusion proteins directly interact with FcγR isoforms. As shown in FIGS. 2A-2E, the recombinant OVA-FLIPr fusion protein and OVA-FLIPr-like fusion protein bound all the tested FcγR isoforms, including FcγRI (FIG. 2A), FcγRIIa-H131 (FIG. 2B), FcγRIIb (FIG. 2C), FcγRIIIa-V158 (FIG. 2D), and FcγRIIIa-F158 (FIG. 2E). In contrast, there was no interaction between the recombinant OVA and the FcγR isoforms. The results were mean±standard error (SEM) of duplicate wells. These results indicate that the antigen fusion protein of the present invention can directly bind to different FcγR isoforms.

Example 2

Immunization with the OVA Fusion Protein Enhances OVA-Specific T-Cell Responses

To ascertain whether the FcγR binding activity of the antigen fusion protein of the present invention associates with the immune responses in vivo, C57BL/6 mice were arbitrarily assigned to groups (6 mice per group) and subcutaneously administered twice with 10 μg of the OVA, the OVA-FLIPr fusion protein, or the OVA-FLIPr-like fusion protein at a two-week interval. The mice administered with PBS alone served as negative controls. One week after the second immunization, the splenocytes of the immunized mice were harvested and examined for the number of IFN-γ-secreting CD4$^+$ and CD8$^+$ T cells by ELISPOT assay.

Figure 3A:
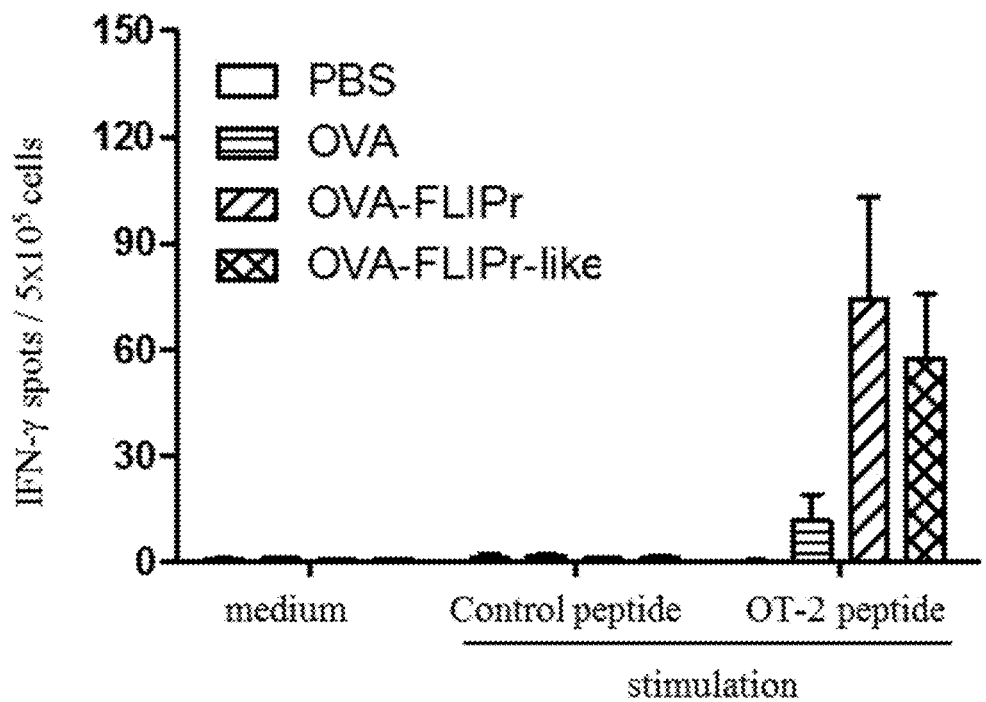
FIG. 3A shows the frequencies of IFN-γ-secreting $CD4^+$ T cells in the peptide-pulsed splenocytes from mice immunized twice with the OVA, the OVA-FLIPr fusion protein, the OVA-FLIPr-like fusion protein, or phosphate buffered saline (PBS)
Figure 3B:
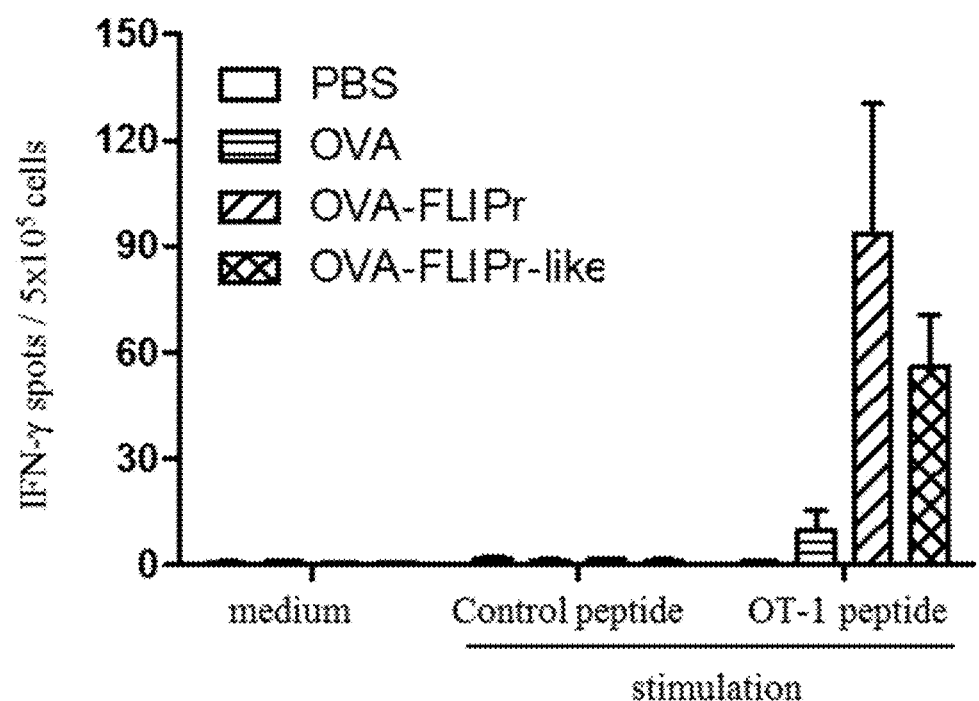
FIG. 3B shows the frequencies of IFN-γ-secreting $CD8^+$ T cells in the peptide-pulsed splenocytes from mice immunized twice with the OVA, the OVA-FLIPr fusion protein, the OVA-FLIPr-like fusion protein, or PBS.

As shown in FIGS. 3A-3B, background levels of IFN-γ-secreting cells were detected from all of the splenocytes without stimulation (medium alone) or stimulated with control peptides. After stimulation with an OT-2 peptide (a CD4$^+$ T cell epitope; FIG. 3A) or an OT-1 peptide (a CD8$^+$ T cell epitope; FIG. 3B), low frequencies of the IFN-γ-secreting cells were observed in the splenocytes of OVA immunized mice. In contrast, the mice immunized with the OVA-FLIPr fusion protein or the OVA-FLIPr-like fusion protein induced high frequencies of IFN-γ-secreting cells. These results indicate that immunization with the antigen fusion protein of the present invention can effectively induce antigen-specific T-cell responses.

Example 3

Immunization with the OVA Fusion Protein Stimulates Cytotoxic Immunity

To investigate whether the antigen fusion protein of the present invention stimulates cytotoxic immunity, an in vivo cytotoxicity assay was performed. C57BL/6 mice were arbitrarily assigned to groups (7-8 mice per group) and administered subcutaneously with 30 μg of the OVA, the OVA-FLIPr fusion protein, or the OVA-FLIPr-like fusion protein two times at a two-week interval. The mice administered with PBS alone served as negative controls. An equal mixture of OT-1 peptide-pulsed splenocytes labeled with high concentration of CFSE (CFSE$^{hig}$) and control peptide-pulsed splenocytes labeled with lower concentration of CFSE (CFSE$^{low}$) were then injected into the immunized mice via an intravenous route. The immunized mice were sacrificed after 24 hours and the killing of the peptide-pulsed splenocytes in spleen by cytotoxic T lymphocytes was analyzed using flow cytometry.

Figure 4A:
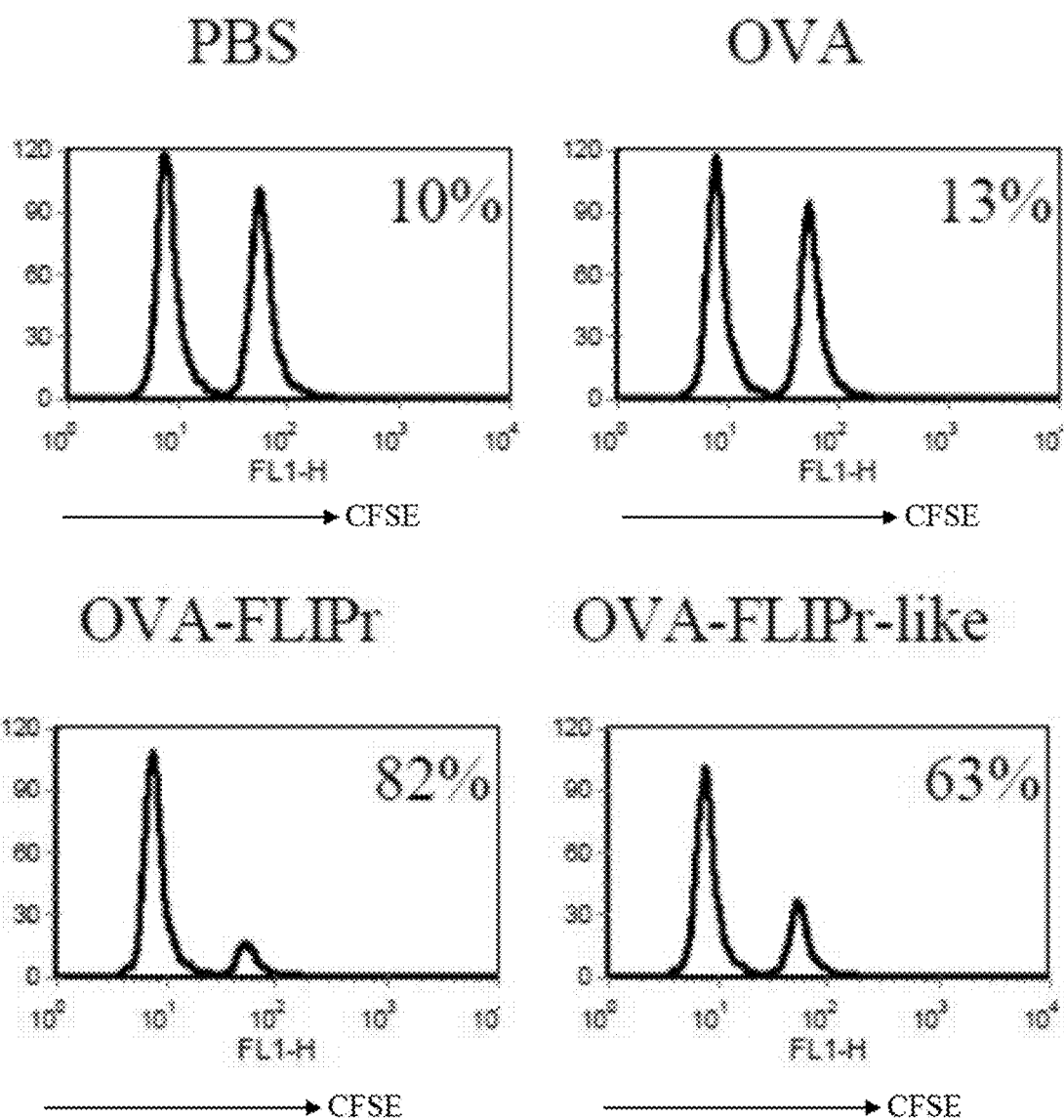
FIG. 4A shows carboxyfluorescein succinimidyl ester (CFSE) profiles of the OT-1 peptide-pulsed splenocytes labeled with high concentration of CFSE from mice immunized twice with the OVA, the OVA-FLIPr fusion protein, the OVA-FLIPr-like fusion protein, or PBS; the percentage shown in each panel represents the percent specific killing in one experiment.
Figure 4B:
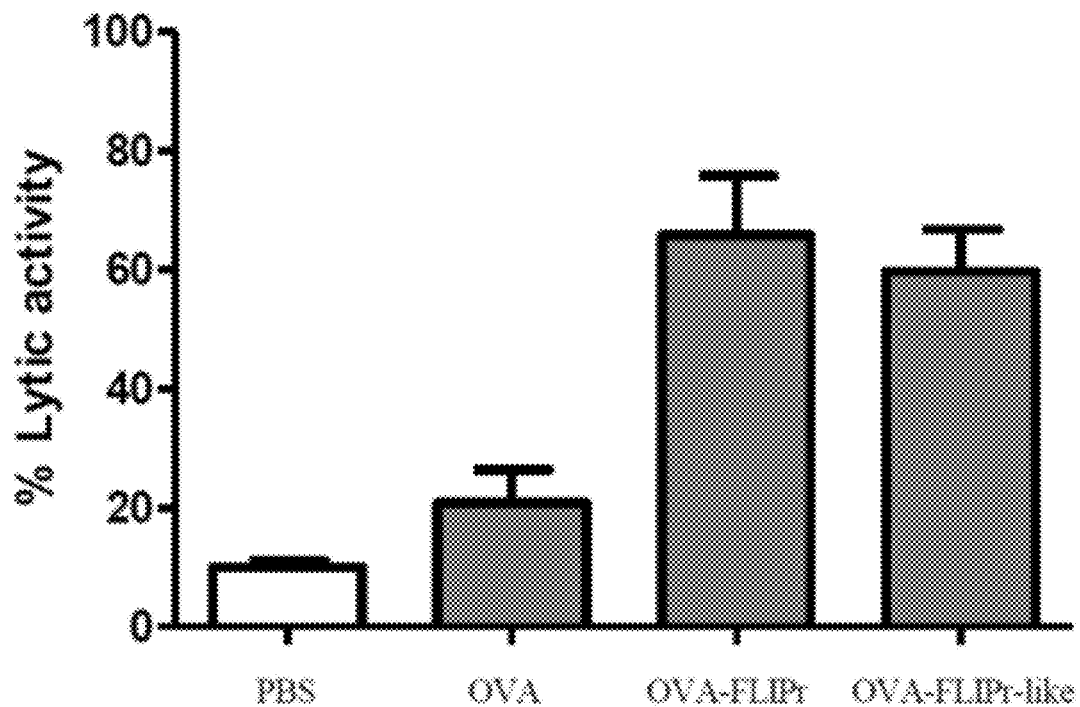
FIG. 4B shows the percent specific killing of the OT-1 peptide-pulsed splenocytes from mice immunized twice with the OVA, the OVA-FLIPr fusion protein, the OVA-FLIPr-like fusion protein, or PBS.

FIG. 4A shows CFSE profiles of the peptide-pulsed splenocytes from each group of the immunized mice. FIG. 4B shows the percent specific killing of the peptide-pulsed splenocytes from each group of the immunized mice. According to FIGS. 4A-4B, less specific killing of the peptide-pulsed splenocytes was observed for the OVA immunized mice. In contrast, the mice immunized with the OVA-FLIPr fusion protein or the OVA-FLIPr-like fusion protein exhibited significantly more killing of the peptide-pulsed splenocytes. These results indicate that immunization with the antigen fusion protein of the present invention can effectively stimulate antigen-specific cytotoxic immunity.

Example 4

Immunization with the OVA Fusion Protein Induces Antitumor Responses

To examine whether the antigen fusion protein of the present invention induces antitumor responses in vivo, C57BL/6 mice were arbitrarily assigned to groups (6 mice per group) and administered twice with 10 μg of the OVA, the OVA-FLIPr fusion protein, or the OVA-FLIPr-like fusion protein at a two-week interval. The mice administered with PBS alone served as negative controls. One week after the second immunization, mice were inoculated subcutaneously on the left flank with $5 \times 10^5$ EG7 tumor cells transfected with an OVA gene and producing OVA constitutively, followed by measurement of the Tumor volume.

Figure 5:
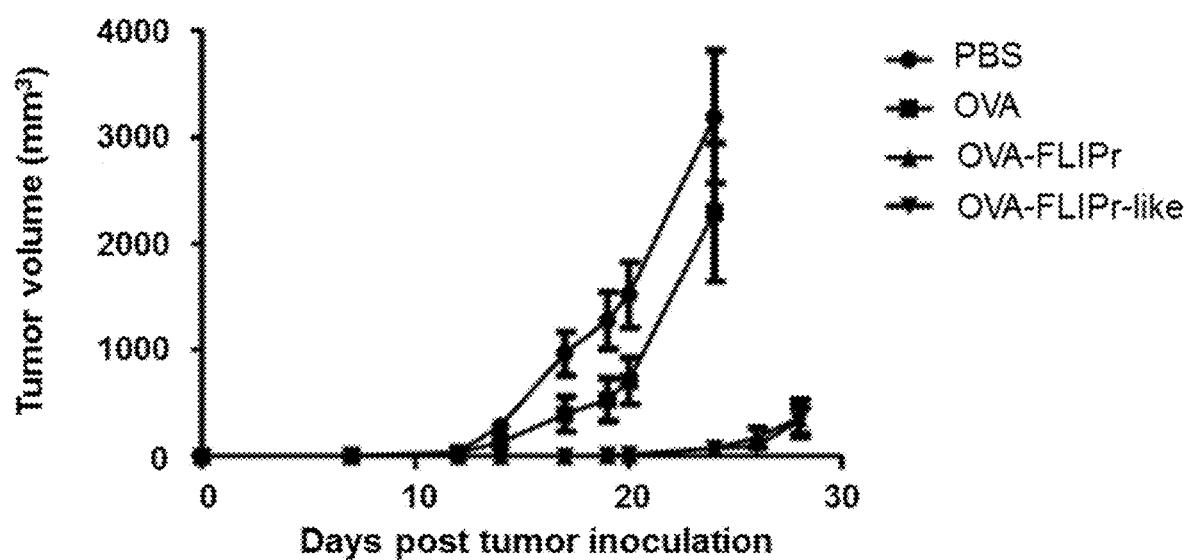
FIG. 5 shows the estimated tumor volume in mice immunized twice with the OVA, the OVA-FLIPr fusion protein, the OVA-FLIPr-like fusion protein, or PBS, and then inoculated with EG7 tumor cells.

As shown in FIG. 5, tumor growth was inhibited in the mice immunized with the OVA-FLIPr fusion protein or the OVA-FLIPr-like fusion protein. In contrast, the mice immunized with the OVA did not show significant reduction of tumor volume when compared with the mice immunized with PBS. These results indicate that immunization with the antigen fusion protein of the present invention can effectively induce antigen-specific antitumor responses in the tumor-bearing subjects.

Example 5

Preparation of the Survivin Fusion Protein

According to the similar procedures described in Example 1, recombinant proteins of survivin, an inhibitor protein to apoptosis, and Sur-FLIPr fusion protein were prepared and analyzed by SDS-PAGE and western blotting.

Figure 6A:
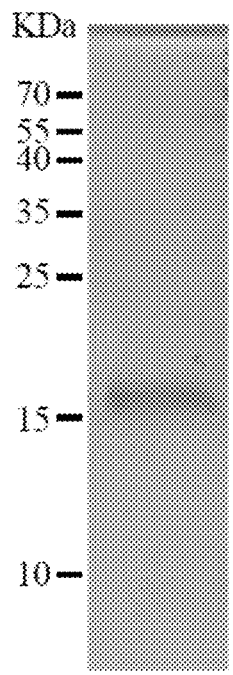
FIGS. 6A-6B show an image of a polyacrylamide gel displaying purified recombinant proteins, including a survivin and a survivin-FLIPr (Sur-FLIPr) fusion protein.
Figure 6B:
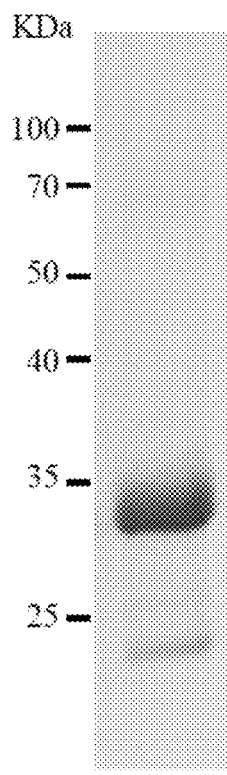
Figure 6C:
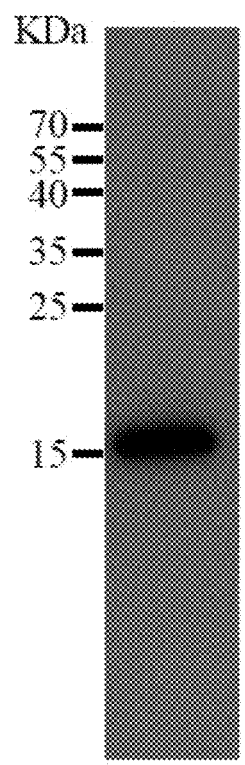
FIGS. 6C-6D show detection of the purified recombinant proteins, including the survivin and the Sur-FLIPr fusion protein, by western blotting using an anti-survivin antibody.
Figure 6D:
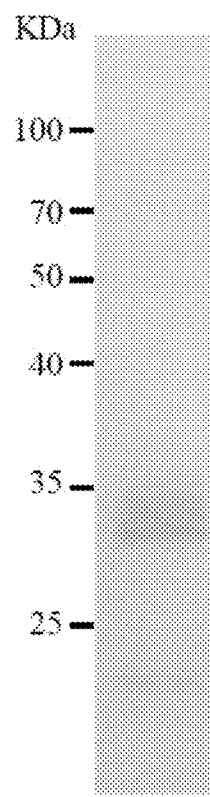
Figure 7A:
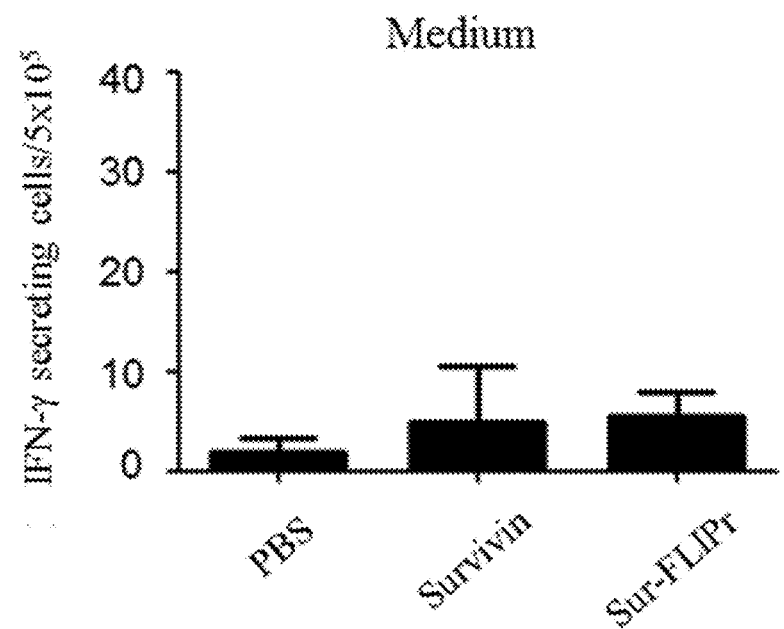
FIG. 7A shows the frequencies of IFN-γ-secreting $CD8^+$ T cells in the medium-pulsed splenocytes from mice immunized twice with the survivin, Sur-FLIPr fusion protein, or PBS.
Figure 7B:
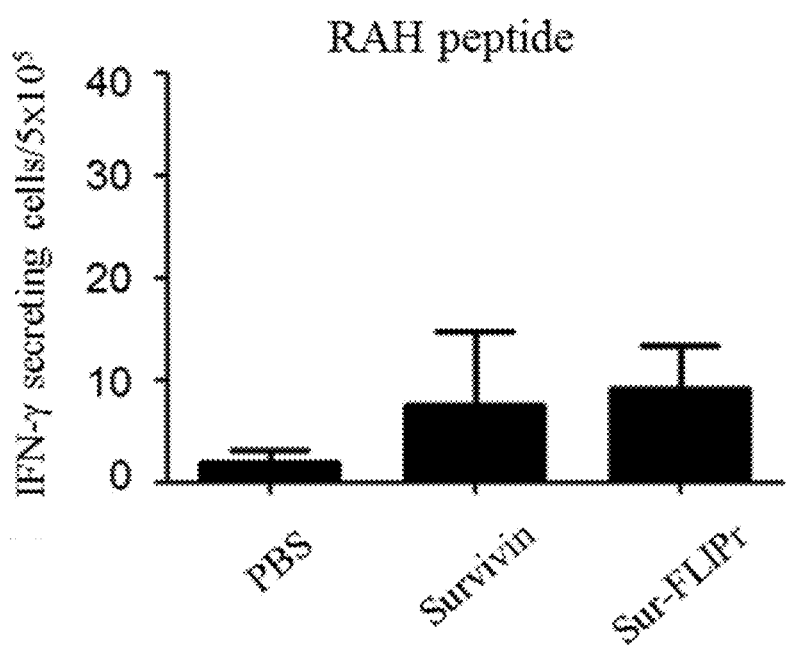
FIG. 7B shows the frequencies of IFN-γ-secreting $CD8^+$ T cells in the RAH peptide-pulsed splenocytes from mice immunized twice with the survivin, Sur-FLIPr fusion protein, or PBS.
Figure 7C:
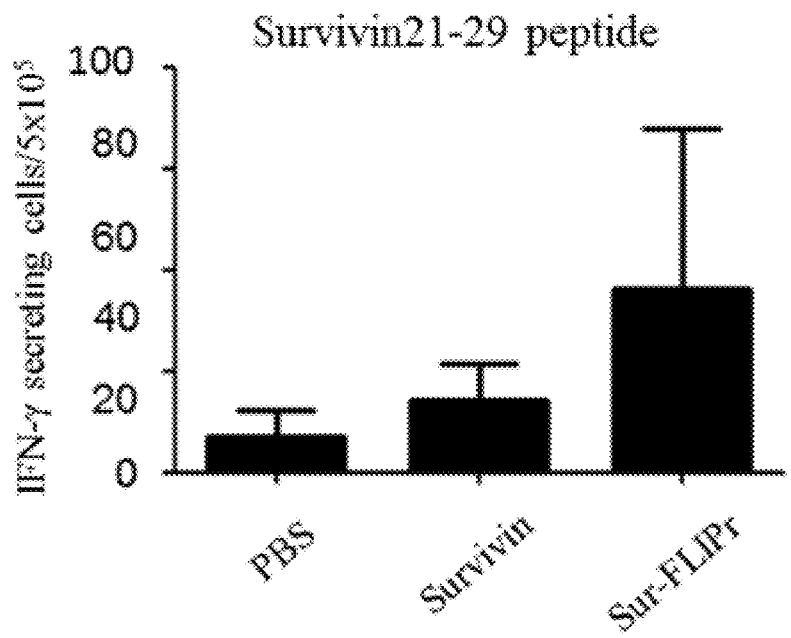
FIG. 7C shows the frequencies of IFN-γ-secreting $CD8^+$ T cells in the survivin21-29 peptide-pulsed splenocytes from mice immunized twice with the survivin, Sur-FLIPr fusion protein, or PBS.
Figure 7D:
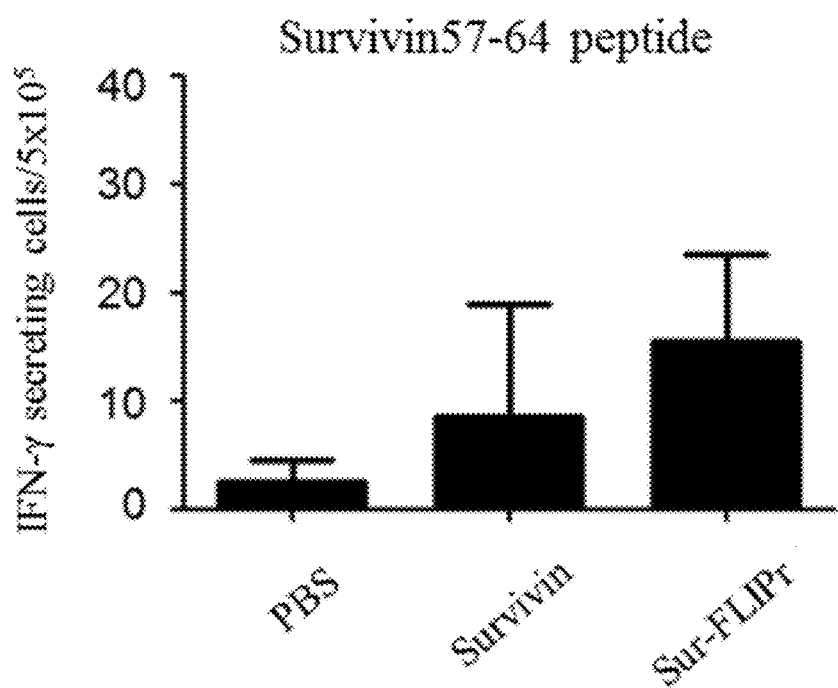
FIG. 7D shows the frequencies of IFN-γ-secreting $CD8^+$ T cells in the survivin57-64 peptide-pulsed splenocytes from mice immunized twice with the survivin, Sur-FLIPr fusion protein, or PBS.

As shown in FIGS. 6A-6B, the recombinant survivin and Sur-FLIPr fusion protein were visualized on the polyacrylamide gel stained with Coomassie brilliant blue. As shown in FIGS. 6C-6D, the recombinant survivin and Sur-FLIPr fusion protein were detected by western blotting using the anti-survivin antibody.

Example 6

Immunization with the Survivin Fusion Protein Enhances Survivin-Specific T-Cell Responses C57BL/6 mice were arbitrarily assigned to groups (6 mice per group) and subcutaneously administered twice with 30 μg of the survivin or the Sur-FLIPr fusion protein at a two-week interval. The mice administered with PBS alone served as negative controls. One week after the second immunization, the splenocytes of the immunized mice were harvested and examined for the number of IFN-γ-secreting CD8$^+$ T cells by ELISPOT assay.

As shown in FIGS. 7A-7D, the background levels of IFN-γ-secreting cells were detected from all of the splenocytes without stimulation (medium alone) or stimulated with a control RAH peptide. After stimulation with a survivin21-29 peptide or a survivin57-64 peptide (CD8$^+$ T cell epitopes), low frequencies of the IFN-γ-secreting cells were observed in the splenocytes of survivin immunized mice. In contrast, the mice immunized with the Sur-FLIPr fusion protein induced high frequencies of IFN-γ-secreting CD8$^+$ T cells. These results indicate that immunization with the antigen fusion protein of the present invention can effectively induce antigen-specific T-cell responses.

Example 7

Immunization with the Survivin Fusion Protein Induces Antitumor Responses

C57BL/6 mice subcutaneously inoculated with 5×10$^4$ EG7 tumor cells were arbitrarily assigned to groups (9-11 mice per group) and administered twice with 30 mg of the survivin or the Sur-FLIPr fusion protein on day 3 and 10 after tumor inoculation. The mice administered with PBS alone served as negative controls. Tumor volume was measured to assess the antitumor activity of the Sur-FLIPr fusion protein.

Figure 8:
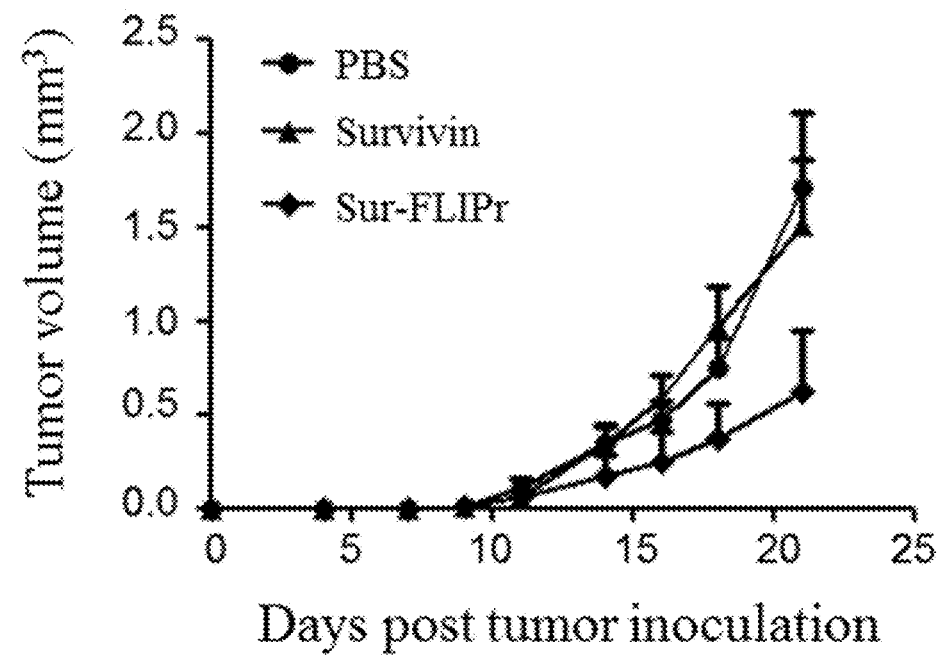
FIG. 8 shows the estimated tumor volume in mice inoculated with EG7 tumor cells and then immunized twice with the survivin, the Sur-FLIPr fusion protein, or PBS.

As shown in FIG. 8, tumor growth was inhibited in the mice immunized with the Sur-FLIPr fusion protein. In contrast, the mice immunized with the survivin did not show significant reduction of tumor volume when compared with the mice immunized with PBS. These results indicate that immunization with the antigen fusion protein of the present invention can effectively induce antitumor responses.

Example 8

Immunization with the Mesothelin Fusion Protein Enhances Mesothelin-Specific T-Cell Responses Recombinant proteins of mesothelin, a protein reported to be overexpressed in tumors such as mesothelioma and ovarian and pancreatic adenocarcinoma, and mesothelin-FLIPr fusion proteins were prepared according to the similar procedures described in Example 1 (data not shown). C57BL/6 mice were arbitrarily assigned to groups (3 mice per group) and subcutaneously administered twice with 10 μg of the mesothelin or the mesothelin-FLIPr fusion protein at a one-week interval. The mice administered with PBS alone served as negative controls. One week after the second immunization, the splenocytes of the immunized mice were isolated and stimulated with 10 μg/mL of the mesothelin for five days, and then the levels of IFN-γ, IL-2, IL-5, and IL-17A secreted into the culture medium were measured by ELISA.

Figure 9:
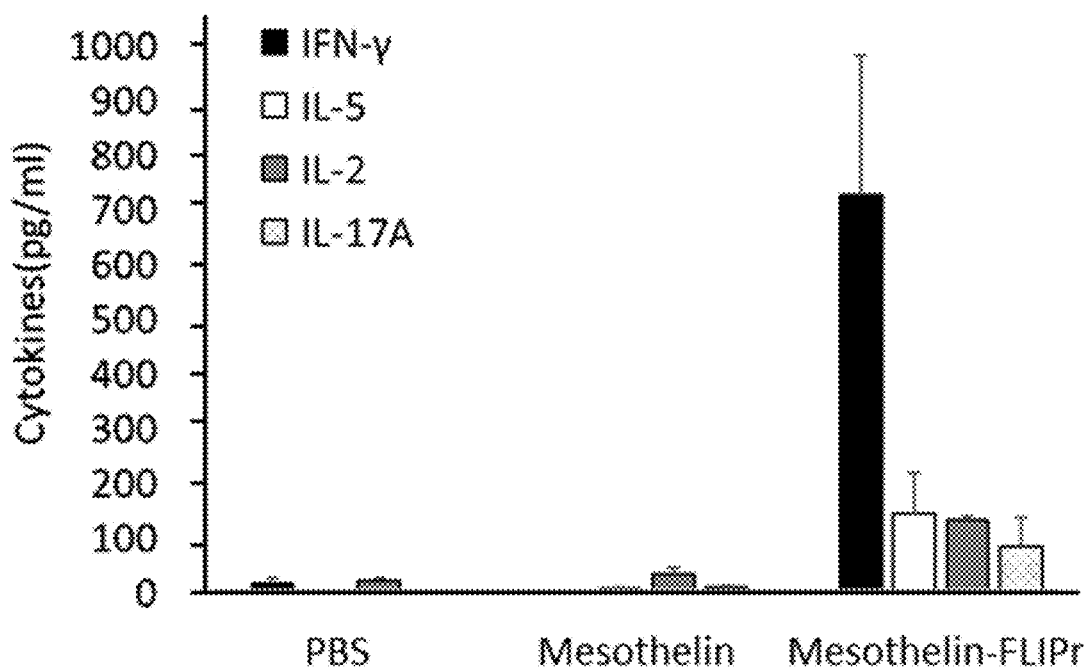
FIG. 9 shows the levels of proinflammatory cytokines secreted by helper T cells in the mesothelin-pulsed splenocytes from mice immunized twice with a recombinant mesothelin, a recombinant mesothelin-FLIPr fusion protein, or PBS; the cytokines include IFN-γ, IL-2, IL-5, and IL-17A.

As shown in FIG. 9, high levels of proinflammatory cytokines, including IFN-γ, IL-2, IL-5, and IL-17, were secreted by helper T cells in the stimulated splenocytes from the mice immunized with the mesothelin-FLIPr fusion protein. In contrast, small amounts of these cytokines were detected in the splenocytes from the mesothelin or PBS-immunized mice. These results indicate that immunization with the antigen fusion protein of the present invention can effectively induce antigen-specific helper T-cell responses.

Example 9

Preparation and FcγR Binding of the ZE3 Fusion Protein

According to the similar procedures described in Example 1, recombinant proteins of ZE3 and ZE3-FLIPr fusion protein were prepared and analyzed by SDS-PAGE and western blotting.

Figure 10A:
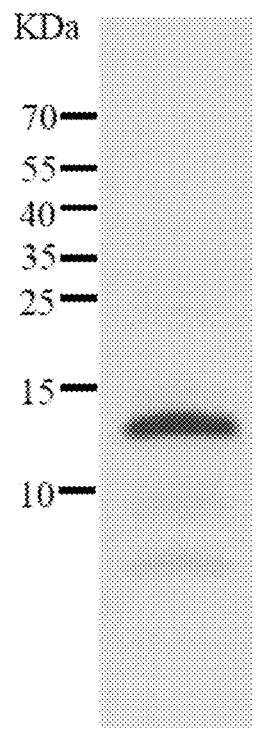
FIGS. 10A-10B show an image of a polyacrylamide gel displaying purified recombinant proteins, including a Zika virus envelope protein domain III (ZE3) and a ZE3-FLIPr fusion protein.
Figure 10B:
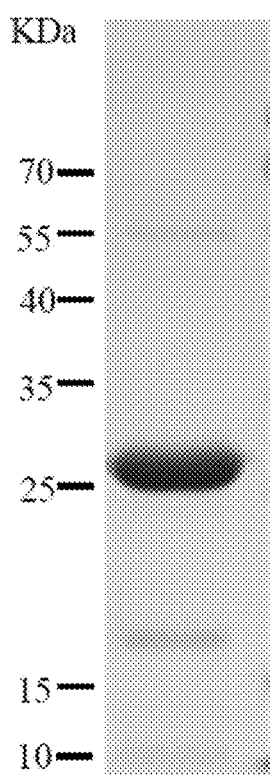
Figure 10C:
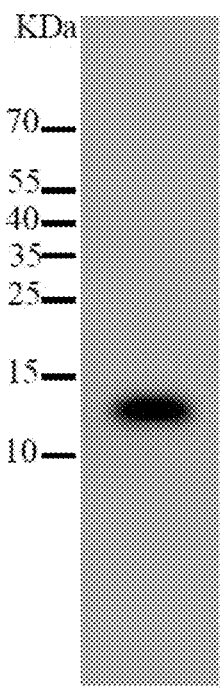
FIGS. 10C-10D show detection of the purified recombinant proteins, including the ZE3 and the ZE3-FLIPr fusion protein, by western blotting using an anti-ZE3 antibody.
Figure 10D:
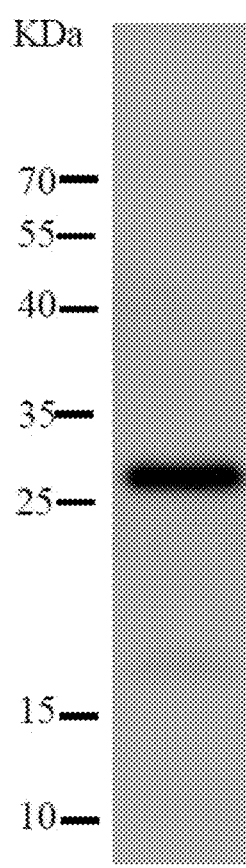

As shown in FIGS. 10A-10B, the recombinant ZE3 and ZE3-FLIPr fusion protein were visualized on the polyacrylamide gel stained with Coomassie brilliant blue. As shown in FIGS. 10C-10D, the recombinant ZE3 and ZE3-FLIPr fusion protein were detected by western blotting using the anti-ZE3 antibody.

Figure 11:
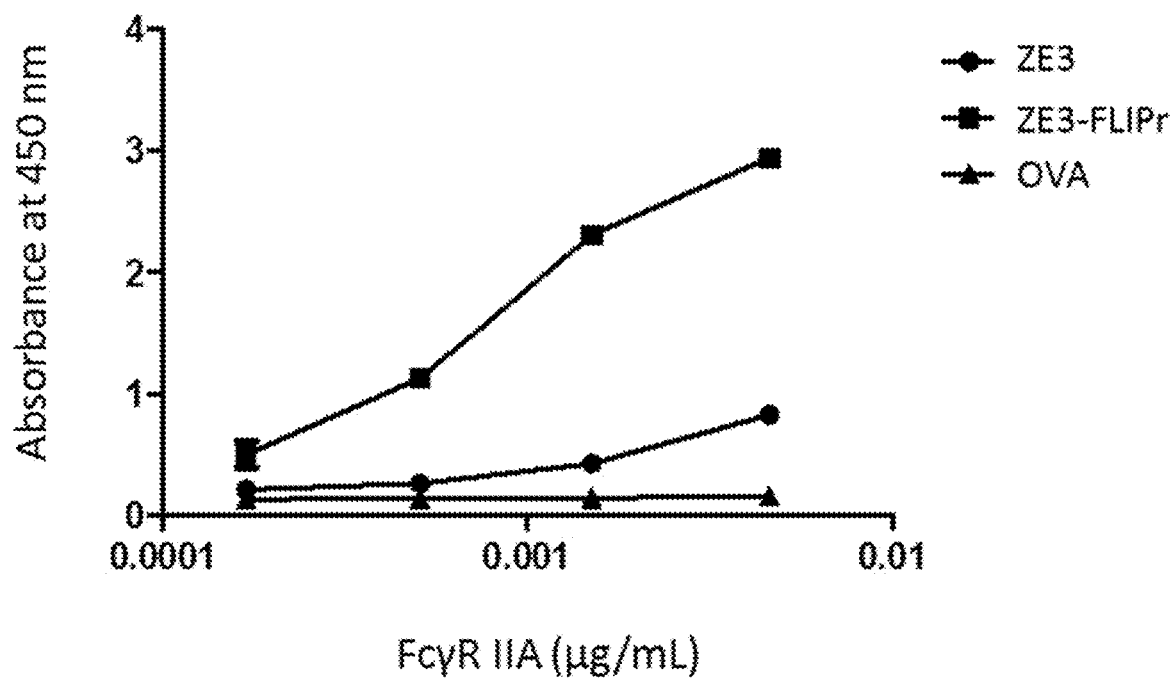
FIG. 11 shows the binding of FcγRIIA to the recombinant proteins, including the ZE3 and the ZE3-FLIPr fusion protein.

To analyze the functional activity of the recombinant ZE3-FLIPr fusion protein, a capture ELISA was performed to confirm the interaction between FcγRIIA and the ZE3-FLIPr fusion protein. As shown in FIG. 11, the binding of FcγRIIA to the recombinant ZE3-FLIPr fusion protein was detected. In contrast, there was weak interaction between the recombinant ZE3 and FcγRIIA. This result demonstrates that the antigen fusion protein of the present invention can directly bind to FcγR.

Example 10

Immunization with the ZE3 Fusion Protein Enhances Antibody Production

C57BL/6 mice were arbitrarily assigned to groups (4 mice per group) and subcutaneously administered twice with 10 μg of the ZE3 or ZE3-FLIPr fusion protein at a two-week interval. Four weeks after the first immunization, the sera of the immunized mice were collected for determination of the titers of anti-ZE3 IgG antibodies using ELISA.

Figure 12:
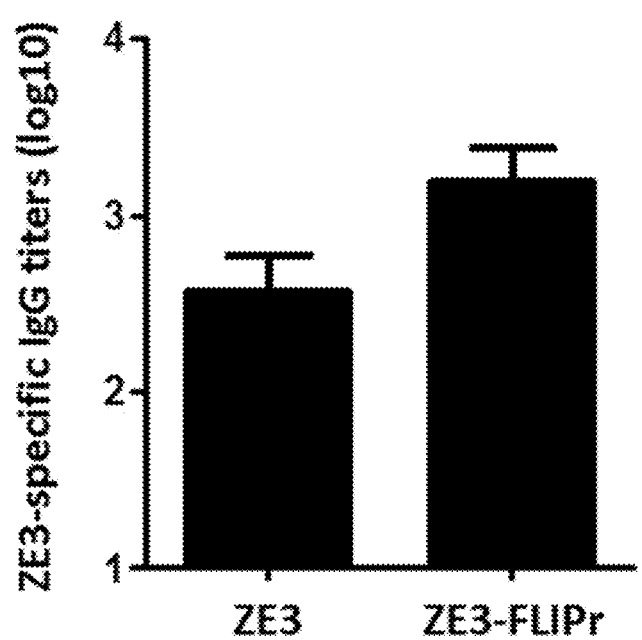
FIG. 12 shows the titers of ZE3-specific IgG antibodies in the sera from mice immunized twice with the ZE3 or the ZE3-FLIPr fusion protein.

As shown in FIG. 12, superior production of the ZE3-specific IgG antibodies were observed in the mice immunized with the ZE3-FLIPr fusion protein. Comparatively, fewer ZE3-specific IgG were produced by the ZE3-immunized mice. These results indicate that immunization with the antigen fusion protein of the present invention can effectively induce antigen-specific antibody production.

In conclusion, the antigen fusion protein of the present invention can induce higher antigen-specific immune responses in a subject than the antigen itself. Therefore, a pharmaceutical composition which contains such antigen fusion protein may be employed in the development of potent vaccines, such as antitumor and antivirus vaccines. The examples of the present invention also demonstrate a simple and direct method of enhancing immunogenicity of an antigen and a method of enhancing immune responses to an antigen in a subject. These methods may increase the efficacy of vaccine antigens and elicit efficient immune responses in subjects with compromised immunity.

What is claimed is:

1. A pharmaceutical composition, comprising an antigen fusion protein comprising an antigen and an antagonist of an Fc gamma receptor, wherein the antagonist of the Fc gamma receptor is a formyl peptide receptor-like 1 inhibitory protein (FLIPr) or a FLIPr-like protein.

2. The pharmaceutical composition of claim 1, wherein the antigen is a polypeptide derived from a cancer cell or a virus.

3. The pharmaceutical composition of claim 2, wherein the polypeptide is selected from the group consisting of survivin, mesothelin, and Zika virus envelope protein domain III.

4. A method of enhancing immunogenicity of an antigen, comprising conjugating the antigen with an antagonist of an Fc gamma receptor to form an antigen fusion protein, wherein the antagonist of the Fc gamma receptor is a FLIPr or a FLIPr-like protein.

5. The method of claim 4, wherein the antigen is a polypeptide derived from a cancer cell or a virus.

6. The method of claim 5, wherein the polypeptide is selected from the group consisting of survivin, mesothelin, and Zika virus envelope protein domain III.

7. A method of enhancing an immune response to an antigen in a subject, comprising administering to the subject an effective amount of an antigen fusion protein, wherein the antigen fusion protein comprises the antigen and an antagonist of an Fc gamma receptor, wherein the antagonist of the Fc gamma receptor is a FLIPr or a FLIPr-like protein.

8. The method of claim 7, wherein the antigen is a polypeptide derived from a cancer cell or a virus.

9. The method of claim 8, wherein the polypeptide is selected from the group consisting of survivin, mesothelin, and Zika virus envelope protein domain III.

10. The method of claim 7, wherein the immune response comprises an increase in $CD4^+$ T cells, $CD8^+$ T cells, or combinations thereof.

11. The method of claim 7, wherein the immune response comprises secretion of a cytokine selected from the group consisting of interferon gamma, interleukin-2, interleukin-5, interleukin-17A, and combinations thereof.

12. The method of claim 7, wherein the immune response comprises production of an antigen-specific immunoglobulin G antibody.

* * * * *

SEQUENCE LISTING

<160> NUMBER OF SEQ ID NOS: 17

<210> SEQ ID NO 1
<211> LENGTH: 105
<212> TYPE: PRT
<213> ORGANISM: Staphylococcus aureus

<400> SEQUENCE: 1

Phe Phe Ser Tyr Glu Trp Lys Gly Leu Glu Ile Ala Lys Asn Leu Ala
1               5                   10                  15

Asp Gln Ala Lys Lys Asp Asp Glu Arg Ile Asp Lys Leu Met Lys Glu
            20                  25                  30

Ser Asp Lys Asn Leu Thr Pro Tyr Lys Ala Glu Thr Val Asn Asp Leu
        35                  40                  45

Tyr Leu Ile Val Lys Lys Leu Ser Gln Gly Asp Val Lys Lys Ala Val
    50                  55                  60

Val Arg Ile Lys Asp Gly Gly Pro Arg Asp Tyr Tyr Thr Phe Asp Leu
65                  70                  75                  80

Thr Arg Pro Leu Glu Glu Asn Arg Lys Asn Ile Lys Val Val Lys Asn
                85                  90                  95

Gly Glu Ile Asp Ser Ile Tyr Trp Asp
            100                 105

<210> SEQ ID NO 2
<211> LENGTH: 104
<212> TYPE: PRT
<213> ORGANISM: Staphylococcus aureus

<400> SEQUENCE: 2

Phe Phe Ser Tyr Glu Trp Lys Gly Leu Glu Ile Ala Lys Asn Leu Ala
1               5                   10                  15

Asp Gln Ala Lys Lys Asp Asp Glu Arg Ala Asp Lys Leu Ile Lys Glu
            20                  25                  30

Ala Asp Glu Lys Asn Glu His Tyr Lys Gly Lys Thr Val Glu Asp Leu
        35                  40                  45

Tyr Val Ile Ala Lys Lys Met Gly Lys Gly Asn Thr Ile Ala Val Val
    50                  55                  60

Lys Ile Lys Asp Gly Gly Lys Asn Gly Tyr Tyr Thr Phe Asp Ile Thr
65                  70                  75                  80

Arg Pro Leu Glu Glu His Arg Lys Asn Ile Pro Val Val Lys Asn Gly
                85                  90                  95

Glu Ile Asp Ser Ile Thr Trp Tyr
            100

<210> SEQ ID NO 3
<211> LENGTH: 394
<212> TYPE: PRT
<213> ORGANISM: Artificial sequence
<220> FEATURE:
<223> OTHER INFORMATION: Recombinant OVA

<400> SEQUENCE: 3

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

-continued

```
Ser Thr Arg Thr Gln Ile Asn Lys Val Val Arg Phe Asp Lys Leu Pro
    50                  55                  60
Gly Phe Gly Asp Ser Ile Glu Ala Gln Cys Gly Thr Ser Val Asn Val
65                  70                  75                  80
His Ser Ser Leu Arg Asp Ile Leu Asn Gln Ile Thr Lys Pro Asn Asp
                85                  90                  95
Val Tyr Ser Phe Ser Leu Ala Ser Arg Leu Tyr Ala Glu Glu Arg Tyr
            100                 105                 110
Pro Ile Leu Pro Glu Tyr Leu Gln Cys Val Lys Glu Leu Tyr Arg Gly
        115                 120                 125
Gly Leu Glu Pro Ile Asn Phe Gln Thr Ala Ala Asp Gln Ala Arg Glu
130                 135                 140
Leu Ile Asn Ser Trp Val Glu Ser Gln Thr Asn Gly Ile Ile Arg Asn
145                 150                 155                 160
Val Leu Gln Pro Ser Ser Val Asp Ser Gln Thr Ala Met Val Leu Val
                165                 170                 175
Asn Ala Ile Val Phe Lys Gly Leu Trp Glu Lys Ala Phe Lys Asp Glu
            180                 185                 190
Asp Thr Gln Ala Met Pro Phe Arg Val Thr Glu Gln Glu Ser Lys Pro
        195                 200                 205
Val Gln Met Met Tyr Gln Ile Gly Leu Phe Arg Val Ala Ser Met Ala
210                 215                 220
Ser Glu Lys Met Lys Ile Leu Glu Leu Pro Phe Ala Ser Gly Thr Met
225                 230                 235                 240
Ser Met Leu Val Leu Leu Pro Asp Glu Val Ser Gly Leu Glu Gln Leu
                245                 250                 255
Glu Ser Ile Ile Asn Phe Glu Lys Leu Thr Glu Trp Thr Ser Ser Asn
            260                 265                 270
Val Met Glu Glu Arg Lys Ile Lys Val Tyr Leu Pro Arg Met Lys Met
        275                 280                 285
Glu Glu Lys Tyr Asn Leu Thr Ser Val Leu Met Ala Met Gly Ile Thr
290                 295                 300
Asp Val Phe Ser Ser Ser Ala Asn Leu Ser Gly Ile Ser Ser Ala Glu
305                 310                 315                 320
Ser Leu Lys Ile Ser Gln Ala Val His Ala Ala His Ala Glu Ile Asn
                325                 330                 335
Glu Ala Gly Arg Glu Val Val Gly Ser Ala Glu Ala Gly Val Asp Ala
            340                 345                 350
Ala Ser Val Ser Glu Glu Phe Arg Ala Asp His Pro Phe Leu Phe Cys
        355                 360                 365
Ile Lys His Ile Ala Thr Asn Ala Val Leu Phe Phe Gly Arg Cys Val
370                 375                 380
Ser Pro Leu Glu His His His His His His
385                 390

<210> SEQ ID NO 4
<211> LENGTH: 514
<212> TYPE: PRT
<213> ORGANISM: Artificial sequence
<220> FEATURE:
<223> OTHER INFORMATION: Recombinant OVA-FLIPr fusion protein

<400> SEQUENCE: 4

Met Gly Ser Ile Gly Ala Ala Ser Met Glu Phe Cys Phe Asp Val Phe
1               5                   10                  15
```

-continued

```
Lys Glu Leu Lys Val His His Ala Asn Glu Asn Ile Phe Tyr Cys Pro
             20                  25                  30
Ile Ala Ile Met Ser Ala Leu Ala Met Val Tyr Leu Gly Ala Lys Asp
         35                  40                  45
Ser Thr Arg Thr Gln Ile Asn Lys Val Val Arg Phe Asp Lys Leu Pro
     50                  55                  60
Gly Phe Gly Asp Ser Ile Glu Ala Gln Cys Gly Thr Ser Val Asn Val
65                  70                  75                  80
His Ser Ser Leu Arg Asp Ile Leu Asn Gln Ile Thr Lys Pro Asn Asp
                 85                  90                  95
Val Tyr Ser Phe Ser Leu Ala Ser Arg Leu Tyr Ala Glu Glu Arg Tyr
            100                 105                 110
Pro Ile Leu Pro Glu Tyr Leu Gln Cys Val Lys Glu Leu Tyr Arg Gly
        115                 120                 125
Gly Leu Glu Pro Ile Asn Phe Gln Thr Ala Ala Asp Gln Ala Arg Glu
    130                 135                 140
Leu Ile Asn Ser Trp Val Glu Ser Gln Thr Asn Gly Ile Ile Arg Asn
145                 150                 155                 160
Val Leu Gln Pro Ser Ser Val Asp Ser Gln Thr Ala Met Val Leu Val
                165                 170                 175
Asn Ala Ile Val Phe Lys Gly Leu Trp Glu Lys Ala Phe Lys Asp Glu
            180                 185                 190
Asp Thr Gln Ala Met Pro Phe Arg Val Thr Glu Gln Glu Ser Lys Pro
        195                 200                 205
Val Gln Met Met Tyr Gln Ile Gly Leu Phe Arg Val Ala Ser Met Ala
    210                 215                 220
Ser Glu Lys Met Lys Ile Leu Glu Leu Pro Phe Ala Ser Gly Thr Met
225                 230                 235                 240
Ser Met Leu Val Leu Leu Pro Asp Glu Val Ser Gly Leu Glu Gln Leu
                245                 250                 255
Glu Ser Ile Ile Asn Phe Glu Lys Leu Thr Glu Trp Thr Ser Ser Asn
            260                 265                 270
Val Met Glu Glu Arg Lys Ile Lys Val Tyr Leu Pro Arg Met Lys Met
        275                 280                 285
Glu Glu Lys Tyr Asn Leu Thr Ser Val Leu Met Ala Met Gly Ile Thr
    290                 295                 300
Asp Val Phe Ser Ser Ser Ala Asn Leu Ser Gly Ile Ser Ser Ala Glu
305                 310                 315                 320
Ser Leu Lys Ile Ser Gln Ala Val His Ala Ala His Ala Glu Ile Asn
                325                 330                 335
Glu Ala Gly Arg Glu Val Val Gly Ser Ala Glu Ala Gly Val Asp Ala
            340                 345                 350
Ala Ser Val Ser Glu Glu Phe Arg Ala Asp His Pro Phe Leu Phe Cys
        355                 360                 365
Ile Lys His Ile Ala Thr Asn Ala Val Leu Phe Phe Gly Arg Cys Val
    370                 375                 380
Ser Pro Gly Gly Gly Ser Gly Gly Gly Gly Ser Gly Gly Gly Gly
385                 390                 395                 400
Ser Phe Phe Ser Tyr Glu Trp Lys Gly Leu Glu Ile Ala Lys Asn Leu
                405                 410                 415
Ala Asp Gln Ala Lys Lys Asp Glu Arg Ile Asp Lys Leu Met Lys
            420                 425                 430
Glu Ser Asp Lys Asn Leu Thr Pro Tyr Lys Ala Glu Thr Val Asn Asp
```

```
                435                 440                 445
Leu Tyr Leu Ile Val Lys Lys Leu Ser Gln Gly Asp Val Lys Lys Ala
    450                 455                 460

Val Val Arg Ile Lys Asp Gly Gly Pro Arg Asp Tyr Tyr Thr Phe Asp
465                 470                 475                 480

Leu Thr Arg Pro Leu Glu Glu Asn Arg Lys Asn Ile Lys Val Val Lys
                485                 490                 495

Asn Gly Glu Ile Asp Ser Ile Tyr Trp Asp Leu Glu His His His His
                500                 505                 510

His His

<210> SEQ ID NO 5
<211> LENGTH: 513
<212> TYPE: PRT
<213> ORGANISM: Artificial sequence
<220> FEATURE:
<223> OTHER INFORMATION: Recombinant OVA-FLIPr-like fusion protein

<400> SEQUENCE: 5

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
                20                  25                  30

Ile Ala Ile Met Ser Ala Leu Ala Met Val Tyr Leu Gly Ala Lys Asp
                35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
                100                 105                 110

Pro Ile Leu Pro Glu Tyr Leu Gln Cys Val Lys Glu Leu Tyr Arg Gly
            115                 120                 125

Gly Leu Glu Pro Ile Asn Phe Gln Thr Ala Ala Asp Gln Ala Arg Glu
        130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
                180                 185                 190

Asp Thr Gln Ala Met Pro Phe Arg Val Thr Glu Gln Glu Ser Lys Pro
            195                 200                 205

Val Gln Met Met Tyr Gln Ile Gly Leu Phe Arg Val Ala Ser Met Ala
        210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
                260                 265                 270

Val Met Glu Glu Arg Lys Ile Lys Val Tyr Leu Pro Arg Met Lys Met
            275                 280                 285
```

```
Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro Gly Gly Gly Ser Gly Gly Gly Ser Gly Gly Gly Gly
385                 390                 395                 400

Ser Phe Phe Ser Tyr Glu Trp Lys Gly Leu Glu Ile Ala Lys Asn Leu
                405                 410                 415

Ala Asp Gln Ala Lys Lys Asp Glu Arg Ala Asp Lys Leu Ile Lys
            420                 425                 430

Glu Ala Asp Glu Lys Asn Glu His Tyr Lys Gly Lys Thr Val Glu Asp
        435                 440                 445

Leu Tyr Val Ile Ala Lys Lys Met Gly Lys Gly Asn Thr Ile Ala Val
    450                 455                 460

Val Lys Ile Lys Asp Gly Gly Lys Asn Gly Tyr Tyr Thr Phe Asp Ile
465                 470                 475                 480

Thr Arg Pro Leu Glu Glu His Arg Lys Asn Ile Pro Val Val Lys Asn
                485                 490                 495

Gly Glu Ile Asp Ser Ile Thr Trp Tyr Leu Glu His His His His
            500                 505                 510

His

<210> SEQ ID NO 6
<211> LENGTH: 151
<212> TYPE: PRT
<213> ORGANISM: Artificial sequence
<220> FEATURE:
<223> OTHER INFORMATION: Recombinant survivin

<400> SEQUENCE: 6

Met Met Gly Ala Pro Thr Leu Pro Pro Ala Trp Gln Pro Phe Leu Lys
1               5                   10                  15

Asp His Arg Ile Ser Thr Phe Lys Asn Trp Pro Phe Leu Glu Gly Cys
                20                  25                  30

Ala Cys Thr Pro Glu Arg Met Ala Glu Ala Gly Phe Ile His Cys Pro
            35                  40                  45

Thr Glu Asn Glu Pro Asp Leu Ala Gln Cys Phe Phe Cys Phe Lys Glu
        50                  55                  60

Leu Glu Gly Trp Glu Pro Asp Asp Pro Ile Glu Glu His Lys Lys
65                  70                  75                  80

His Ser Ser Gly Cys Ala Phe Leu Ser Val Lys Lys Gln Phe Glu Glu
                85                  90                  95

Leu Thr Leu Gly Glu Phe Leu Lys Leu Asp Arg Glu Arg Ala Lys Asn
            100                 105                 110

Lys Ile Ala Lys Glu Thr Asn Asn Lys Lys Glu Phe Glu Glu Thr
        115                 120                 125
```

```
Ala Lys Lys Val Arg Arg Ala Ile Glu Gln Leu Ala Ala Met Asp Leu
    130                 135                 140

Glu His His His His His
145                 150

<210> SEQ ID NO 7
<211> LENGTH: 258
<212> TYPE: PRT
<213> ORGANISM: Artificial sequence
<220> FEATURE:
<223> OTHER INFORMATION: Recombinant survivin-FLIPr fusion protein

<400> SEQUENCE: 7

Met Met Gly Ala Pro Thr Leu Pro Pro Ala Trp Gln Pro Phe Leu Lys
1               5                   10                  15

Asp His Arg Ile Ser Thr Phe Lys Asn Trp Pro Phe Leu Glu Gly Cys
                20                  25                  30

Ala Cys Thr Pro Glu Arg Met Ala Glu Ala Gly Phe Ile His Cys Pro
            35                  40                  45

Thr Glu Asn Glu Pro Asp Leu Ala Gln Cys Phe Phe Cys Phe Lys Glu
        50                  55                  60

Leu Glu Gly Trp Glu Pro Asp Asp Pro Ile Glu Glu His Lys Lys
65                  70                  75                  80

His Ser Ser Gly Cys Ala Phe Leu Ser Val Lys Lys Gln Phe Glu Glu
                85                  90                  95

Leu Thr Leu Gly Glu Phe Leu Lys Leu Asp Arg Glu Arg Ala Lys Asn
            100                 105                 110

Lys Ile Ala Lys Glu Thr Asn Asn Lys Lys Glu Phe Glu Thr
        115                 120                 125

Ala Lys Lys Val Arg Arg Ala Ile Glu Gln Leu Ala Ala Met Asp Leu
    130                 135                 140

Asp Phe Phe Ser Tyr Glu Trp Lys Gly Leu Gly Ile Ala Lys Asn Leu
145                 150                 155                 160

Ala Asp Gln Ala Lys Lys Asp Glu Arg Ile Asp Lys Leu Met Lys
            165                 170                 175

Glu Ser Asp Lys Asn Leu Thr Pro Tyr Lys Ala Glu Thr Val Asn Asp
        180                 185                 190

Leu Tyr Leu Ile Val Lys Lys Leu Ser Gln Gly Asp Val Lys Lys Ala
    195                 200                 205

Val Val Arg Ile Lys Asp Gly Gly Pro Arg Asp Tyr Tyr Thr Phe Asp
210                 215                 220

Leu Thr Arg Pro Leu Glu Glu Asn Arg Lys Asn Ile Lys Val Val Lys
225                 230                 235                 240

Asn Gly Glu Ile Asp Ser Ile Tyr Trp Asp Leu Glu His His His His
            245                 250                 255

His His

<210> SEQ ID NO 8
<211> LENGTH: 312
<212> TYPE: PRT
<213> ORGANISM: Artificial sequence
<220> FEATURE:
<223> OTHER INFORMATION: Recombinant mesothelin

<400> SEQUENCE: 8

Met Asp Ala Glu Gln Lys Ala Cys Pro Pro Gly Lys Glu Pro Tyr Lys
1               5                   10                  15
```

Val Asp Glu Asp Leu Ile Phe Tyr Gln Asn Trp Glu Leu Glu Ala Cys
            20                  25                  30

Val Asp Gly Thr Met Leu Ala Arg Gln Met Asp Leu Val Asn Glu Ile
            35                  40                  45

Pro Phe Thr Tyr Glu Gln Leu Ser Ile Phe Lys His Lys Leu Asp Lys
 50                  55                  60

Thr Tyr Pro Gln Gly Tyr Pro Glu Ser Leu Ile Gln Gln Leu Gly His
 65                  70                  75                  80

Phe Phe Arg Tyr Val Ser Pro Glu Asp Ile His Gln Trp Asn Val Thr
                85                  90                  95

Ser Pro Asp Thr Val Lys Thr Leu Leu Lys Val Ser Lys Gly Gln Lys
                100                 105                 110

Met Asn Ala Gln Ala Ile Ala Leu Val Ala Cys Tyr Leu Arg Gly Gly
                115                 120                 125

Gly Gln Leu Asp Glu Asp Met Val Lys Ala Leu Gly Asp Ile Pro Leu
    130                 135                 140

Ser Tyr Leu Cys Asp Phe Ser Pro Gln Asp Leu His Ser Val Pro Ser
145                 150                 155                 160

Ser Val Met Trp Leu Val Gly Pro Gln Asp Leu Asp Lys Cys Ser Gln
                165                 170                 175

Arg His Leu Gly Leu Leu Tyr Gln Lys Ala Cys Ser Ala Phe Gln Asn
                180                 185                 190

Val Ser Gly Leu Glu Tyr Phe Glu Lys Ile Lys Thr Phe Leu Gly Gly
                195                 200                 205

Ala Ser Val Lys Asp Leu Arg Ala Leu Ser Gln His Asn Val Ser Met
210                 215                 220

Asp Ile Ala Thr Phe Lys Arg Leu Gln Val Asp Ser Leu Val Gly Leu
225                 230                 235                 240

Ser Val Ala Glu Val Gln Lys Leu Leu Gly Pro Asn Ile Val Asp Leu
                245                 250                 255

Lys Thr Glu Glu Asp Lys Ser Pro Val Arg Asp Trp Leu Phe Arg Gln
                260                 265                 270

His Gln Lys Asp Leu Asp Arg Leu Gly Leu Gly Leu Gln Gly Gly Ile
                275                 280                 285

Pro Asn Gly Tyr Leu Val Leu Asp Phe Asn Val Arg Glu Ala Phe Ser
                290                 295                 300

Leu Glu His His His His His His
305                 310

<210> SEQ ID NO 9
<211> LENGTH: 436
<212> TYPE: PRT
<213> ORGANISM: Artificial sequence
<220> FEATURE:
<223> OTHER INFORMATION: Recombinant mesothelin-FLIPr fusion protein

<400> SEQUENCE: 9

Met Asp Ala Glu Gln Lys Ala Cys Pro Pro Gly Lys Glu Pro Tyr Lys
 1               5                   10                  15

Val Asp Glu Asp Leu Ile Phe Tyr Gln Asn Trp Glu Leu Glu Ala Cys
            20                  25                  30

Val Asp Gly Thr Met Leu Ala Arg Gln Met Asp Leu Val Asn Glu Ile
            35                  40                  45

Pro Phe Thr Tyr Glu Gln Leu Ser Ile Phe Lys His Lys Leu Asp Lys
 50                  55                  60

```
Thr Tyr Pro Gln Gly Tyr Pro Glu Ser Leu Ile Gln Gln Leu Gly His
 65                  70                  75                  80

Phe Phe Arg Tyr Val Ser Pro Glu Asp Ile His Gln Trp Asn Val Thr
                 85                  90                  95

Ser Pro Asp Thr Val Lys Thr Leu Leu Lys Val Ser Lys Gly Gln Lys
            100                 105                 110

Met Asn Ala Gln Ala Ile Ala Leu Val Ala Cys Tyr Leu Arg Gly Gly
        115                 120                 125

Gly Gln Leu Asp Glu Asp Met Val Lys Ala Leu Gly Asp Ile Pro Leu
    130                 135                 140

Ser Tyr Leu Cys Asp Phe Ser Pro Gln Asp Leu His Ser Val Pro Ser
145                 150                 155                 160

Ser Val Met Trp Leu Val Gly Pro Gln Asp Leu Asp Lys Cys Ser Gln
                165                 170                 175

Arg His Leu Gly Leu Leu Tyr Gln Lys Ala Cys Ser Ala Phe Gln Asn
            180                 185                 190

Val Ser Gly Leu Glu Tyr Phe Glu Lys Ile Lys Thr Phe Leu Gly Gly
        195                 200                 205

Ala Ser Val Lys Asp Leu Arg Ala Leu Ser Gln His Asn Val Ser Met
    210                 215                 220

Asp Ile Ala Thr Phe Lys Arg Leu Gln Val Asp Ser Leu Val Gly Leu
225                 230                 235                 240

Ser Val Ala Glu Val Gln Lys Leu Leu Gly Pro Asn Ile Val Asp Leu
                245                 250                 255

Lys Thr Glu Glu Asp Lys Ser Pro Val Arg Asp Trp Leu Phe Arg Gln
            260                 265                 270

His Gln Lys Asp Leu Asp Arg Leu Gly Leu Gly Leu Gln Gly Gly Ile
        275                 280                 285

Pro Asn Gly Tyr Leu Val Leu Asp Phe Asn Val Arg Glu Ala Phe Ser
    290                 295                 300

Lys Leu Gly Gly Gly Gly Ser Gly Gly Gly Ser Gly Gly Gly Gly
305                 310                 315                 320

Ser Glu Phe Phe Phe Ser Tyr Glu Trp Lys Gly Leu Glu Ile Ala Lys
                325                 330                 335

Asn Leu Ala Asp Gln Ala Lys Lys Asp Asp Glu Arg Ile Asp Lys Leu
            340                 345                 350

Met Lys Glu Ser Asp Lys Asn Leu Thr Pro Tyr Lys Ala Glu Thr Val
        355                 360                 365

Asn Asp Leu Tyr Leu Ile Val Lys Lys Leu Ser Gln Gly Asp Val Lys
    370                 375                 380

Lys Ala Val Val Arg Ile Lys Asp Gly Gly Pro Arg Asp Tyr Tyr Thr
385                 390                 395                 400

Phe Asp Leu Thr Arg Pro Leu Glu Glu Asn Arg Lys Asn Ile Lys Val
                405                 410                 415

Val Lys Asn Gly Glu Ile Asp Ser Ile Tyr Trp Asp Leu Glu His His
            420                 425                 430

His His His His
        435

<210> SEQ ID NO 10
<211> LENGTH: 115
<212> TYPE: PRT
<213> ORGANISM: Artificial sequence
<220> FEATURE:
<223> OTHER INFORMATION: Recombinant ZE3
```

<400> SEQUENCE: 10

Met Lys Gly Val Ser Tyr Ser Leu Cys Thr Ala Ala Phe Thr Phe Thr
1               5                   10                  15

Lys Ile Pro Ala Glu Thr Leu His Gly Thr Val Thr Val Glu Val Gln
                20                  25                  30

Tyr Ala Gly Thr Asp Gly Pro Cys Lys Val Pro Ala Gln Met Ala Val
            35                  40                  45

Asp Met Gln Thr Leu Thr Pro Val Gly Arg Leu Ile Thr Ala Asn Pro
50                  55                  60

Val Ile Thr Glu Ser Thr Glu Asn Ser Lys Met Met Leu Glu Leu Asp
65                  70                  75                  80

Pro Pro Phe Gly Asp Ser Tyr Ile Val Ile Gly Val Gly Glu Lys Lys
                85                  90                  95

Ile Thr His His Trp His Arg Ser Gly Ser Thr Leu Glu His His His
            100                 105                 110

His His His
        115

<210> SEQ ID NO 11
<211> LENGTH: 239
<212> TYPE: PRT
<213> ORGANISM: Artificial sequence
<220> FEATURE:
<223> OTHER INFORMATION: Recombinant ZE3-FLIPr fusion protein

<400> SEQUENCE: 11

Met Lys Gly Val Ser Tyr Ser Leu Cys Thr Ala Ala Phe Thr Phe Thr
1               5                   10                  15

Lys Ile Pro Ala Glu Thr Leu His Gly Thr Val Thr Val Glu Val Gln
                20                  25                  30

Tyr Ala Gly Thr Asp Gly Pro Cys Lys Val Pro Ala Gln Met Ala Val
            35                  40                  45

Asp Met Gln Thr Leu Thr Pro Val Gly Arg Leu Ile Thr Ala Asn Pro
50                  55                  60

Val Ile Thr Glu Ser Thr Glu Asn Ser Lys Met Met Leu Glu Leu Asp
65                  70                  75                  80

Pro Pro Phe Gly Asp Ser Tyr Ile Val Ile Gly Val Gly Glu Lys Lys
                85                  90                  95

Ile Thr His His Trp His Arg Ser Gly Ser Thr Lys Leu Gly Gly Gly
            100                 105                 110

Gly Ser Gly Gly Gly Ser Gly Gly Gly Ser Glu Phe Phe
        115                 120                 125

Ser Tyr Glu Trp Lys Gly Leu Glu Ile Ala Lys Asn Leu Ala Asp Gln
    130                 135                 140

Ala Lys Lys Asp Asp Glu Arg Ile Asp Lys Leu Met Lys Glu Ser Asp
145                 150                 155                 160

Lys Asn Leu Thr Pro Tyr Lys Ala Glu Thr Val Asn Asp Leu Tyr Leu
                165                 170                 175

Ile Val Lys Lys Leu Ser Gln Gly Asp Val Lys Lys Ala Val Val Arg
            180                 185                 190

Ile Lys Asp Gly Gly Pro Arg Asp Tyr Tyr Thr Phe Asp Leu Thr Arg
        195                 200                 205

Pro Leu Glu Glu Asn Arg Lys Asn Ile Lys Val Val Lys Asn Gly Glu
    210                 215                 220

```
Ile Asp Ser Ile Tyr Trp Asp Leu Glu His His His His His
225                 230                 235
```

<210> SEQ ID NO 12
<211> LENGTH: 8
<212> TYPE: PRT
<213> ORGANISM: Artificial sequence
<220> FEATURE:
<223> OTHER INFORMATION: OT-1 peptide

<400> SEQUENCE: 12

```
Ser Ile Ile Asn Phe Glu Lys Leu
1               5
```

<210> SEQ ID NO 13
<211> LENGTH: 17
<212> TYPE: PRT
<213> ORGANISM: Artificial sequence
<220> FEATURE:
<223> OTHER INFORMATION: OT-2 peptide

<400> SEQUENCE: 13

```
Ile Ser Gln Ala Val His Ala Ala His Ala Glu Ile Asn Glu Ala Gly
1               5                   10                  15

Arg
```

<210> SEQ ID NO 14
<211> LENGTH: 9
<212> TYPE: PRT
<213> ORGANISM: Artificial sequence
<220> FEATURE:
<223> OTHER INFORMATION: RAH peptide

<400> SEQUENCE: 14

```
Arg Ala His Tyr Asn Ile Val Thr Phe
1               5
```

<210> SEQ ID NO 15
<211> LENGTH: 15
<212> TYPE: PRT
<213> ORGANISM: Artificial sequence
<220> FEATURE:
<223> OTHER INFORMATION: Control peptide for OT-2 peptide

<400> SEQUENCE: 15

```
Gly Arg Leu Ile Thr Val Asn Pro Ile Val Thr Glu Lys Asp Ser
1               5                   10                  15
```

<210> SEQ ID NO 16
<211> LENGTH: 9
<212> TYPE: PRT
<213> ORGANISM: Artificial sequence
<220> FEATURE:
<223> OTHER INFORMATION: Survivin21-29

<400> SEQUENCE: 16

```
Thr Phe Lys Asn Trp Pro Phe Leu Glu
1               5
```

<210> SEQ ID NO 17
<211> LENGTH: 8
<212> TYPE: PRT
<213> ORGANISM: Artificial sequence
<220> FEATURE:
<223> OTHER INFORMATION: Survivin57-64

<400> SEQUENCE: 17

```
Cys Phe Phe Cys Phe Lys Glu Leu
1               5
```